(12) United States Patent
Rich

(10) Patent No.: US 7,709,258 B2
(45) Date of Patent: *May 4, 2010

(54) HIGH THROUGHPUT ASSAY FOR IDENTIFYING COMPOUNDS CAPABLE OF MODULATING THE PROLIFERATIVE STATUS OF STEM CELLS

(75) Inventor: Ivan N. Rich, Colorado Springs, CO (US)

(73) Assignee: HemoGenix, Inc., Colorado Springs, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 12/049,861

(22) Filed: Mar. 17, 2008

(65) Prior Publication Data
US 2008/0160564 A1 Jul. 3, 2008

Related U.S. Application Data

(62) Division of application No. 10/059,521, filed on Jan. 29, 2002, now Pat. No. 7,354,729.

(60) Provisional application No. 60/264,796, filed on Jan. 29, 2001.

(51) Int. Cl.
*C12N 5/00* (2006.01)

(52) U.S. Cl. .................... 435/375; 435/2; 435/3; 435/6; 435/8; 435/40.51; 435/374; 435/377; 435/384; 435/385; 435/387; 435/388; 435/392; 436/501; 436/18; 436/63; 436/147

(58) Field of Classification Search .............. 435/1.2, 435/1.3, 2, 3, 7.2, 8, 40.51, 40.52, 7.23, 7.24, 435/7.92, 374–377, 384–388, 391, 392, 6; 436/501, 503, 17, 18, 63, 64, 147, 813
See application file for complete search history.

(56) References Cited

U.S. PATENT DOCUMENTS

| | | | | |
|---|---|---|---|---|
| 5,328,844 | A * | 7/1994 | Moore | 435/405 |
| 5,580,724 | A * | 12/1996 | Alter | 435/6 |
| 5,641,641 | A | 6/1997 | Wood | 435/8 |
| 5,733,541 | A | 3/1998 | Taichman et al. | 424/93.1 |
| 5,814,471 | A | 9/1998 | Wood | 435/8 |
| 5,854,010 | A | 12/1998 | Denison et al. | 435/8 |
| 6,440,407 | B1 | 8/2002 | Bauer et al. | 424/85.1 |
| 6,824,973 | B2 | 11/2004 | Tang et al. | 435/4 |
| 7,354,729 | B2 * | 4/2008 | Rich | 435/8 |
| 7,354,730 | B2 | 4/2008 | Rich | 435/8 |
| 2002/0120098 | A1 * | 8/2002 | Bell et al. | 530/300 |

FOREIGN PATENT DOCUMENTS

| | | |
|---|---|---|
| WO | WO92/13063 | 8/1992 |
| WO | WO94/17177 | 8/1994 |
| WO | WO98/08537 | 3/1998 |
| WO | WO98/21313 | 5/1998 |
| WO | WO98/28437 | 7/1998 |
| WO | WO03/004995 | 1/2003 |
| WO | WO2004/018996 | 3/2004 |

OTHER PUBLICATIONS

Crouch et al. (The Use of ATP Bioluminescence as a Measure of Cell Proliferation and Cytotoxicity, Journal of Immunological Methods, 160: 81-88 (1993).*
Castello et al., Azidothymidine and Interferon-α In Vitro Effects on Hematopoiesis, Experimental Hematology 23: 1367-1371 (1995).*
Aardal, N.P., et al., "Circadian variations in mouse bone marrow", *Exp. Hematol.*, 11(9): 792-801 (1983).
Aardal, N.P., "Circannual variations of circadian periodicity in murine colony-forming cells", *Exp. Hematol.*, 12:61-37 (1984).
Abkowitz, J., et al., "Cyclic hematopoiesis in dogs: Studies of erythroid burst-forming cells confirm an early stem cell defect", *Exp. Hematol.*, 16:941-945 (1988).
Abraham, N.G., "Hematopoietic effects of benzene inhalation assessed by long-term bone marrow culture", *Environ Health Perspect*, 104(Suppl 6):1277-1282 (1996).
Abrahamsen, J.F., et al., "Circadian cell cycle vaiations of erythro- and myelopoiesis in humans", *Eur. J. Haematol.*, 58(5):333-345 (1997). [Abstract Only].
Ballmaier, M., et al., "c-mpl mutations are the cause of congenital amegakaryocytic thrombocytopenia", *Blood*, 97:139-146 (2001).
Baudoux, E., et al., "Circadian and seasonal variations of hematopoiesis in cord blood", *Bone Marrow Transplantation*, 22(Suppl 1):S12 (1998).

(Continued)

*Primary Examiner*—Gailene R Gabel
(74) *Attorney, Agent, or Firm*—Donna E. Becker

(57) ABSTRACT

The present invention relates generally to high-throughput assay methods that determine the proliferative status of hematopoietic stem and progenitor cells. The present invention further relates to high-throughput assays for screening compounds that modulate the growth of hematopoietic stem and progenitor cells and for identifying subpopulations thereof that are suitable for transplantation. The assay of the present invention is particularly useful for quality control and monitoring of the growth potential in the stem cell transplant setting and would provide improved control over the reconstitution phase of transplanted cells.

30 Claims, 11 Drawing Sheets

OTHER PUBLICATIONS

Botta, M., et al., "Toxicity on human hemopoietic progenitors of 2'-2'-difluoro-2' deoxycytidine (gemcitabine)", *Anticancer Research*, 18:1037-1042 (1998).

Bradbury, D.A., et al., "Measuremenet of the ADP:ATP ratio in human leukaemic cell lines can be used as an indicator of cell viability, necrosis and apoptosis", *Journal of Immunological Methods*, 240:79-92 (2000).

Bradley, T.R., et al., "The growth of mouse bone marrow cells in vitro", *Aust. J. Exp. Biol. Med. Sci.*, 44:287-300 (1966).

Bradley, T.R., et al., "The effect of oxyen tension on haemopoietic and fibroblast cell proliferation in vitro", *J. Cell. Physiol.*, 97:517-522 (1978).

Bulanova, E.G., et al., "Bioluminescent assay for human lymphocyte blast transformation", *Immunol. Lett.*, 46(1-2):153-155 (1995).

Carulli, G., et al., "Cyclic oscillations of neutrophils, monocytes, and CD8-positive lymphocytes in a healthy subject", *Haematologica*, 85(4):447-448 (2000).

Castello, G., et al., "Azidothymidine and interferon-α in vitro effects on hematopoiesis: Protective in vitro activity of IL-1 and GM-CSF", *Experimental Hematology*, 23:1367-1371 (1995).

Cerruti, A., et al., "Hematotoxicity of 5-fluorouracil-leucovorin in a setting of adjuvant chemotherapy", *Anticancer Research*, 14:2163-2166 (1994).

Clement, M., et al., "Chemopreventive agent resveratrol, a natural product derived from grapes, triggers CD95 signaling-dependent apoptosis in human tumor cells", *Blood*, 92(3):996-1002 (1998).

Corsini, C., et al., "Idarubicinol myelotoxicity: A comparison of in vitro data with clinical outcome in patients treated with high-dose idarubicin", *British Journal of Cancer*, 82(3):524-528 (2000).

Crouch, S.P.M., et al., "The use of ATP bioluminescence as a measure of cell proliferation and cytotoxicity", *Journal of Immunological Methods*, 160:81-88 (1993).

Doz, F., et al., "Experimental basis for increasing the therapeutic index of carboplatin in brain tumor therapy by pretreatment with WR compounds", *Cancer Chemother. Pharmacol.*, 28:308-310 (1991).

Farris, G., et al., "Benzene-induced hematotoxicity and bone marrow compensation in B6C3F1 mice", *Fundamental and Applied Toxicology*, 36:119-129 (1997).

Fujisaki, T., et al., "Rapid differentiation of a rare subset of adult human Lin⁻CD34⁻CD38⁻ cells stimulated by multiple growth factors in vitro", *Blood*, 94(6):1926-1932 (1999).

Gabbianelli, M., et al., "Multi-level effects of flt3 ligand on human hematopoiesis: Expansion of putative stem cells and proliferation of granulomonocytic progenitors/monocytic precursors", *Blood*, 86(5):1661-1670 (1995).

Ghielmini, M., et al., "Hematotoxicity on human bone marrow—and umbilical cord blood-derived progenitor cells and in vitro therapeutic index of methoxymorpholinyldoxorubicin and its metabolites", *Cancer Chemother. Pharmacol.*, 42:235-240 (1998).

Ghielmini, M., et al., "In vitro schedule-dependency of myelotoxicity and cytotoxicity of Ecteinascidin 743 (ET-743)", *Annals of Oncology*, 9:989-993 (1998).

Ghielmini, M., et al., "Differential toxicity of anticancer drugs on late (GM-CFC) and early (LTC-IC) hemopoietic progenitors in vitro", *Cell Biology and Toxicology*, 15:395-404 (1999).

Gribaldo, L., et al., "Inhibition of CFU-E/BFU-E by 3'—azido-3'—deoxythymidine, chlorpropamide, and protoporphirin IX zinc (II): a comparison between direct exposure of progenitor cells and long-term exposure of bone marrow cultures", *Toxicological Sciences*, 58:96-101 (2000).

Haurie, C., et al., "Hematopoietic dynamics in grey collies", *Experimental Hematology*, 27:1139-1148 (1999).

Hodgson, G.S., et al., "The organization of hemopoietic tissue as inferred from the effects of 5-fluorouracil", *Exp. Hematol.*, 10(1):26-35 (1982).

Hodgson, G.S., et al., "In vitro production of CFU-S and cells with erythropoiesis repopulating ability by 5-fluorouracil treated mouse bone marrow", *International Journal of Cell Cloning*, 1:49-56 (1983).

Hohl, R.J., "Monoterpenes as regulators of malignant cell proliferation", *Adv. Exp. Med. Biol.*, 401:137-146 (1996).

Holt, D.E., et al., "The myelotoxicity of chloramphenicol: in vitro and in vivo studies: I. In vitro effects on cells in culture", *Hum. Exp. Toxicol.*, 16(10):570-576 (1997).

Horowitz, D., et al., "Colorimetric determination of inhibition of hematopoietic progenitor cells in soft agar", *Journal of Immunological Methods*, 244:49-58 (2000).

Iscove, N.N., et al., "Erythroid colony formation in cultures of mouse and human bone marrow: analysis of the requirement for erythropoietin by gel filtration and affinity chromatography on agarose-concanavalin A", *J. Cell. Physiol.*, 83:309-320 (1974).

Katayama, Y., et al., "Replating potential of colony-forming units of granulocytes/macrophages (CFU-GM) expanded ex vivo by stem cell factor, interleukin (IL)-3, IL-6, granulocyte colony-stimulating factor, erythropoietin with or without thrombopoietin", *Int. J. Hematol.*, 68(2):157-168 (1998).

Konwalinka, G., et al., "A miniaturized agar culture system for cloning human erythropoietic progenitor cells", *Exp. Hematol.*, 12:75-79 (1984).

Kravtsov, V., et al., "Use of the microculture kinetic assay of apoptosis to determine chemosensitivities of leukemias", *Blood*, 92(3):968-980 (1998).

Laerum, O.D., et al., "Chronobiological aspects of bone marrow and blood cells", *Prog. Clin. Biol. Res.*, 59C:87-97 (1981).

Laerum, O,D., "Hematopoiesis occurs in rhythms", *Experimental Hematology*, 23:1145-1147 (1995).

Lerza, R., et al., "In vitro toxicity of a 3'-azido-3'-deoxythymidine and hydroxyurea combination on normal myeloid progenitors", *Anticancer Research*, 18:2755-2758 (1998).

Maddens, S., et al., "Kit signaling inhibits the sphingomyelin-ceramide pathway through $PLC_\gamma 1$: Implication in stem cell factor radioprotective effect", *Blood*, 100(4):1294-1301 (2002).

McLeod, D., et al., "Improved plasma culture system for production of erythrocytic colonies in vitro: Quantitative assay method for CFU-E", *Blood*, 44 (4):517-534 (1974).

Mosmann, T., "Rapid colorimetric assay for cellular growth and survival: Application to proliferation and cytotoxicity assays", *Journal of Immunological Methods*, 65:55-63 (1983).

Noé, G., et al., "A sensitive sandwich ELISA for measuring erythropoietin in human serum", *Br. J. Haematol.*, 80(3):285-292 (1992).

Parchment, R.E., et al., "Predicting hematological toxicity (myelosuppression) of cytotoxic drug therapy from in vitro tests", *Ann. Oncol.*, 9(4):357-364 (1998).

Parchment, R.E., et al., "Roles for in vitro myelotoxicity tests in preclinical drug development and clinical trial planning", *Toxicol. Pathol.*, 21(2):241-250 (1993). [Abstract Only].

Parent-Massin, D., et al., "In vitro study of pesticide hematotoxicity in human and rat progenitors", *Journal of Pharmacological and Toxicological Methods*, 30(4):203-207 (1993).

Ploemacher, R., et al., "Use of limiting-dilution type long-term marrow cultures in frequency analysis of marrow-repopulating and spleen colony-forming hematopoietic stems cells in the mouse", *Blood*, 78(10):2527-2533 (1991).

Pluznik, D.H., et al., "The induction of clones of normal mast cells by a substance from conditioned medium", *Experimental Cell Research*, 43:553-563 (1966).

Pragnell, I.B., et al., "The effect of stem cell proliferation regulators demonstrated with an in vitro assay", *Blood*, 72(1):196-201 (1988).

Prieto, P., "ECVAM's in-house prevalidation/validation studies in the areas of haematotoxicity, reproductive toxicity, metabolism-mediated toxicity and epithelial barrier function", *The Science of the Total Environment*, 247:349-354 (2000).

Rich, I.N., "The effect of 5-fluorouracil on erythropoiesis", *Blood*, 77(6):1164-1170 (1991).

Rich, I.N., et al., "The effect of reduced oxygen tension on colony formation of erythropoietic cells in vitro", *British Journal of Haematology*, 52:579-588 (1982).

Rich, I.N., et al., "Specific enhancement of mouse CFU-E by mouse transferrin", *Br. J. Haematol.*, 49(4):567-573 (1981). [Abstract Only].

Rich, I.N., et al., "HALO -a multifunctional colony-forming based assay platform for drug development and basic and clinical research", Abstracts of the American Society of Hematology 44th annual meeting, *Blood*, 100(11 Pt 1):1a-1016a (2002). [Abstract Only].

Rich, I.N., et al., "Validation and development of a predictive paradigm for hemotoxicology using a multifunctional bioluminescence colony-forming proliferation assay", *Toxicological Sciences*, 87(2): 427-441 (2005).

Rosendaal, M., et al., "Haemopoietic stem cells are organised for use on the basis of their generation-age", *Nature*, 264:68-69 (1976).

Scheving, L., et al., "Circadian variation in cell division of the mouse alimentary tract, bone marrow and corneal epithelium", *Anat. Rec.*, 191:479-486 (1978).

Smith, M, et al., "Biomarkers of leukemia risk: Benzene as a model", *Environmental Health Perspectives*, 106(4): 937-946 (1998).

Snyder, R., et al., "The toxicology of benzene", *Environmental Health Perspectives*, 100:293-306 (1993).

Sottong, P.R., et al., "Measurement of T-Lymphocyte responses in whole-blood cultures using newly synthesized DNA and ATP", *Clinical and Diagnostic Laboratory Immunology*, 7(2): 307-311 (2000).

Stenn, K.S., et al., "What controls hair follicle cycling?", *Exp. Dermatol.*, 8:229-236 (1999).

Wood, P., et al , "Distinct circadian time structures characterize myeloid and erythroid progenitor and multipotential cell clonogenicity as well as marrow precursor proliferation dynamics", *Experimental Hematology*, 26:523-533 (1998).

Zanello, S., et al., "Expression of the circadian clock genes clock and period1 in human skin", *J. Invest. Dermatol.*, 115:757-760 (2000).

Zimmermann, F., et al., "The sensitivity of in vitro erythropoietic progenitor cells to different erythropoietin reagents during development and the role of cell death in culture", *Exp. Hematol.*, 24(2):330-339 (1996). [Abstract Only].

* cited by examiner

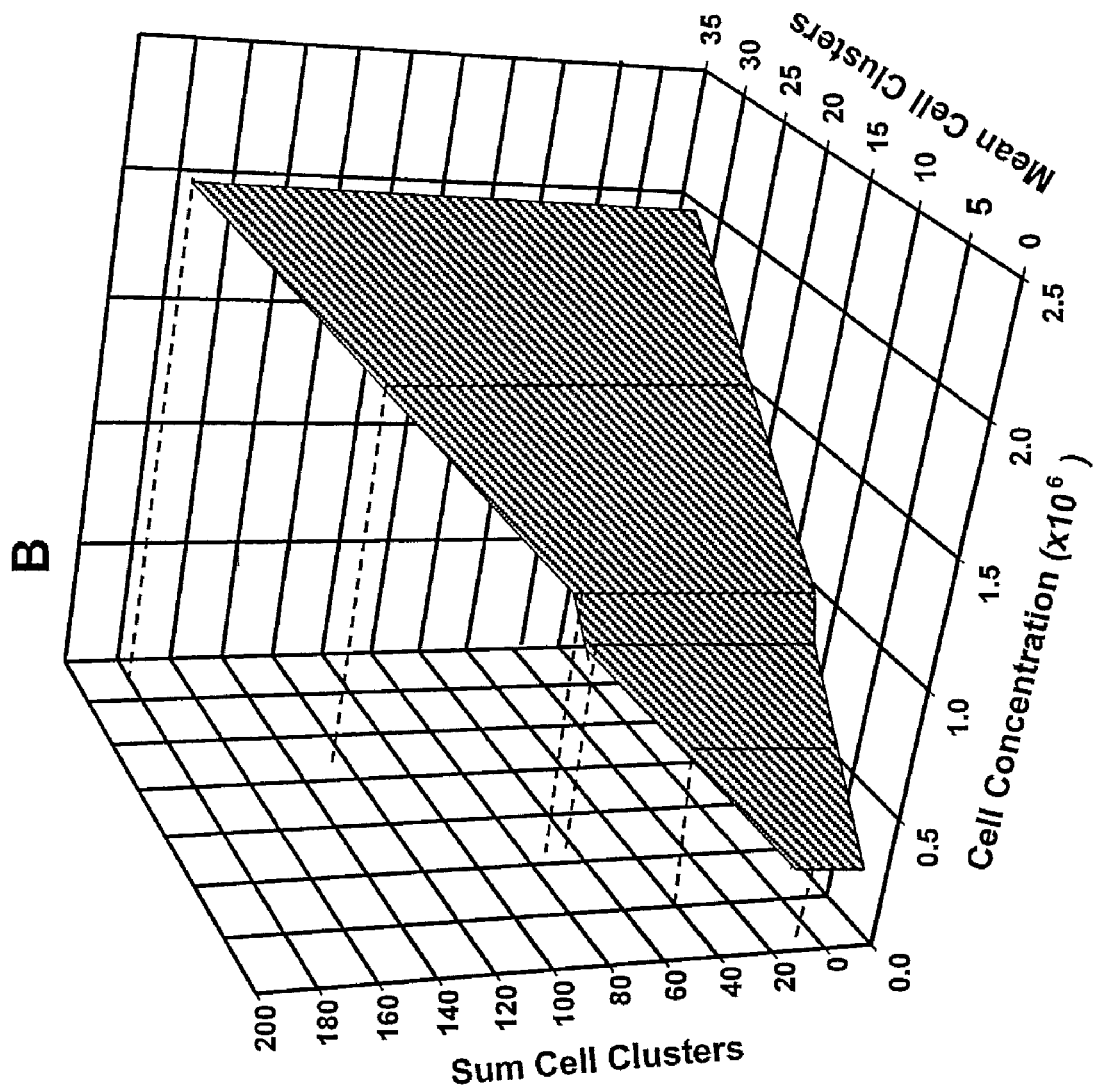

HIGH THROUGHPUT ASSAY FOR IDENTIFYING COMPOUNDS CAPABLE OF MODULATING THE PROLIFERATIVE STATUS OF STEM CELLS

PRIORITY CLAIM

This application claims priority as a divisional application under 35 U.S.C. §120 to U.S. patent application Ser. No. 10/059,521, filed on Jan. 29, 2002, now U.S. Pat. No. 7,354,729, which claims the benefit of U.S. Provisional Patent Application Ser. No. 60/264,796, filed on Jan. 29, 2001. The contents of each of these applications is hereby incorporated by reference in its entirety.

This invention was made with government support under Small Business Innovation Research (SBIR) grant number 1R43CA93244-02 awarded by the NIH. The government has certain rights in the invention.

FIELD OF THE INVENTION

The present invention relates generally to high-throughput assay methods that determine the proliferative status of hematopoietic stem and progenitor cells. The present invention further relates to high-throughput assays for screening compounds that modulate the proliferation of hematopoietic stem and progenitor cells and for identifying subpopulations thereof that are suitable for transplantation.

BACKGROUND

Two major concerns in drug development are the need to predict the efficacy and safety of a potential drug candidate before clinical trials are initiated, and how to predict which individual cancer cases are going to respond to a particular treatment. During the development process, therefore, drug candidates are typically batch tested on a variety of cell lines. Those that seem to have the desired effect on the cell lines are then tested in animals during the preclinical phase. Neither process, however, replicates the true clinical situation. As a result, patients in clinical trials often have to endure unpleasant and sometimes harmful effects because neither differential sensitivity nor patient variability was adequately considered during the drug developmental phases.

To overcome these deficiencies, in vitro cell-based assays that demonstrate a high degree of predictability during different phases of drug development are needed. In addition, there is a need for high throughput assays for screening large numbers of potential drug candidates produced during the discovery phase of drug development and allow those demonstrating promise to continue further in research and development. It therefore follows that assays based on primary cells exhibiting a high degree of predictability, coupled with a high-throughput component, could have a significant impact and value on the drug development process.

The hematopoietic system is one of five continuously proliferating systems of the body, the others being the epithelial mucosa of the gastrointestinal tract, the dermis of the skin, the germ cells of the reproductive organs and the epithelium of the eye cornea. All five proliferating systems share common characteristics, the most important being that a small population of stem cells maintains the continuous production of mature end cells. They all possess the same structural organization of four basic compartments, namely the stem cell, amplification and differentiation, maturation and mature cell compartments.

The hematopoietic system, however, is unique in several ways. It is the only system capable of producing at least eight functionally different cell lineages from a single pluripotent stem cell. Assays are available that allow the differential effect of drugs on the various lympho-hematopoietic lineages to be examined. Second, the site of cell production changes during ontological development. This helps in differential sensitivity testing. Third, the site of production in the adult is the bone marrow, which is a significantly different tissue from the functional site of the peripheral circulation. Fourth, compared with other proliferating systems, and almost all other systems of the body, adult hematopoietic stem and progenitor cells are readily accessible.

Hematopoietic stem and progenitor cell lineages can be used to measure parameters that would normally be inaccessible. For example, the functional site of hematopoiesis is the circulation and mature end cells can be readily obtained to measure red and white blood cell counts, differential counts and other end stage blood parameters. These parameters are conventionally used in preclinical drug testing and form the basis of the National Cancer Institute (NCI) guidelines for hemotoxicity testing during clinical trials. However, these parameters have little if any predictive value as to, for example, the cytotoxic effect of therapeutic compounds on primitive hematopoietic cells or the stem cells of other proliferating tissues.

Besides the mature red and white blood cells, the peripheral blood also contains circulating populations of stem and progenitor cells that can be isolated and used for hematopoietic status monitoring and hemotoxicity testing. The so-called granulocyte-macrophage colony-forming cell (GM-CFC) assay and the enumeration of $CD34^+$ cells (stem and early progenitor cells) currently form the basis of quality control for hematopoietic stem cell transplantation.

The widespread use of in vitro hematopoietic assays was initiated when soluble factors released by fibroblasts were shown to be capable of stimulating cells to form granulocyte-macrophage colonies in soft agar (Bradley & Metcalf, *Aust. J. Exp. Biol. Med.* 44, 287-287 (1987); Pluznik & Sachs, *Exp. Cell Res.* 43, 553-553 (1966)). Colony forming assays (CFAs) for erythropoietic progenitor cells (McLeod et al., *Blood* 44, 617-534 (1974); Iscove et al., *J. Cell Phyisol.* 2-23 (1974); Axelrad et al., *Haemopiesis in Culture* 226-223 (1974)) and other hematopoietic lineages were also developed. The use of cytotoxic drugs such as 5-fluorouracil (Hodgson et al., *Exp. Hemat.* 10, 26-36 (1982) and *Int. J. Cell Cloning* 1, 49-56 (1983)) and hydroxyurea (Rosendaal et al., *Nature* 264, 68-69 (1976)) allowed the hierarchy within the stem cell compartment to be elucidated and in vitro assays for primitive stem cell populations to be developed (Ploemacher et al., *Blood* 78, 2527-2536 (1991); Sutherland et al., *Blood* 72, 104a (1988)).

In vivo, an insult at the stem or early progenitor cell level requires a certain amount of time for the effect to be detected at the peripheral blood level. The effect may not be observed for weeks, or even months. This does not provide a high level of predictability and is why end stage cell parameters cannot be used to predict the effect of an agent. By the time the effect is observed, adverse reactions by the patient have already occurred.

In vitro colony-forming assays based on stem or progenitor cells, on the other hand, can fulfill the requirements of prediction and sensitivity because they detect the effect of the insult before it is observed in the circulation. Colony-forming assays for leukemic cells are also available. In these classic assays, the more primitive the cell to be detected, the longer it takes to detect its progeny in the form of a colony. The proliferative potential of the cells being analyzed, and their ability to be stimulated by growth factors in vitro are essential for these assays. This dependency on the amplification compartment inherent in the hematopoietic system is often overlooked and without this component colony-forming assays in general, and especially predictive hemotoxicity testing, could not be performed.

Under steady-state conditions, the proliferative status of primitive stem cells is considered to be quiescent, while the proportion of cells in cell cycle increases with stem cell maturity. Once the stem cell has become determined with respect to a cell lineage, it enters the amplification compartment for producing the large and constant number of mature cells. With entry into the cell cycle, however, the cell becomes vulnerable to exogenous agents including the cytotoxic drugs typically used in oncology. Thus, the GM-CFC assay, for example, has been used to predict myelosuppression (Prieto, P., Sci. Total Environ. 247, 349-354 (2000)). The predictive quality of this assay, has been proven by validation studies with alkylating agents (Parchment et al., Toxicol. Pathol. 21, 241-250 (1993)). Additionally, however, if the maximum tolerated drug concentration for hematopoietic cells can be predicted, hemotoxicity studies would play an important role in drug discovery since it would be a therapeutic index-based assay (Parchment et al., Ann. Oncol. 9, 357-364 (1998)).

In the case of cytotoxic drug testing, the target cells have to be in cell cycle. For any drug that relies on cell proliferation, the tissues most affected or damaged by toxicity are those actively engaged in cell proliferation, which includes the bone marrow and the gastrointestinal tract. It therefore follows that hemotoxicity testing could also usefully be extrapolated to, and predictive for, the effects of a potential drug on other proliferating tissues.

Toxicity in general, and hemotoxicity in particular, can also be correlated with the time of drug administration. The therapeutic index of a drug, and hence its toxicity, is dependent, in part on the circadian variation in the hematopoietic cell division of rodents (Laerum, O. D., Exp. Hematol. 23, 1145-1147 (1995); Aardal et al., Exp. Hemtol., 11, 792-801 (1993); Aardal, Exp. Hematol. 12, 61-67 (1984); Wood et al., Exp. Hematol., 26, 523-533 (1998)), dogs (Haurie et al., Exp. Hematol. 27, 1139-1148 (1999); Abkowitz et al., Exp. Hematol. 16, 941-945 (1988)) and in humans (Abrahamsen et al., Eur. J. Haematol. 58, 333-345 (1997); Baudoux et al., Bone Marrow Transplant 22 (Suppl. 1) S 12 (1998); Carulli et al., Hematologica 85, 447-448 (2000)). Similarly, cells of the gut mucosa (Schering et al., Anat. Rec. 191, 479-486 (1978)), Stenn & Paus, Exp. Dermatol. 8, 229-233 (1999); Zanello et al., J. Invest. Dermatol. 115, 757-760 (2000)) and the corneal epithelium of the eye (Schening et al., Anat. Rec. 191, 479-486 (1978)) exhibit circadian organization. For human bone marrow and gastrointestinal tissues, for example, S-phase DNA synthesis preferentially occurs in the morning hours rather than in the evening or nighttime hours. This implies cytotoxic agents might be less toxic and exhibit high efficacy if given at a time when the proliferative status of the cells is at a nadir in these tissues.

For toxicity testing, large numbers of comparative samples are needed, thereby making the enumeration of manual CFAs for this purpose impractical. CFAs also suffer from a lack of standardized colony enumeration procedures, and the subjectivity and high degree of expertise of the personnel and the time required for accurate enumeration of the colonies. The long culture periods required to visualize the proliferative potential of different cell populations is also a disadvantage. However, the culture period is an inherent property of the cell population and cannot be changed.

Conventional cell proliferation assays have measured either $^3$H-thymidine or 5-bromo-deoxyuridine (BrdU) incorporation. The BrdU assay can use microscopy, flow cytometry or absorbance. Colorimetric tetrazolium compounds, in particular 3-[4,5-dimethylthiazol-2-yl]-2,5-diphenyltetrazolium bromide (MTT), (Mosmann, J. Immunol. Meth. 65, 666 (1983)), have also been used. Horowitz and King, J. Immunol. Meth. 244, 49-58 (2000)) developed a multi-well, murine colony-forming assay in soft agar whereby the enumeration of cell proliferation or inhibition was measured using the MTT calorimetric method. Results were equivalent to the colony-forming assay. The number of target cells was reduced to $1.25 \times 10^4$ cells/ml, but only studied granulocyte/macrophage progenitor cells were tested and not stem cells, erythropoietic or megakaryopoietic progenitor cells. However, it is also desirable to have an assay system that can accommodate the complete range of target cell populations that can be cultured and subjected to drug-induced hemotoxicity effects.

Hematological malignancies rank 5th and 6th in the cause of deaths for men and women respectively and use of stem cell transplants using peripheral blood, bone marrow and umbilical cord blood have increased dramatically. Reconstitution of the patient after a transplant, however, usually occurs in about 14 days, which is the same time required for the conventional, manual, CFA to detect the growth potential of transplanted cells. Therefore, the usefulness of the GM-CFC assay as an indicator and quality control measure for the growth potential of the transplantable cells is limited. Reliance is often placed on measuring the number of CD34+ cells by flow cytometry, even though this provides no information as to the cell growth potential. Therefore, there is a need for a sensitive, rapid and cost-effective assay that can be used as an indicator for hematopoietic engraftment and reconstitution potential. The patient would benefit significantly because, if engraftment and reconstitution of the lympho-hematopoietic system does not occur after transplantation, the physician can rapidly detect this rejection and proceed with a second transplant, offering reduced financial implications in lower hospitalization and medication costs and improved patient comfort and recovery.

These and other objectives and advantages of the invention will become fully apparent from the description and claims that follow or may be learned by the practice of the invention.

SUMMARY OF THE INVENTION

Briefly described, the present invention relates generally to high-throughput assay methods that determine the proliferative status of hematopoietic stem and progenitor cells. The present invention further relates to high-throughput assays for screening compounds that modulate the growth of hematopoietic stem and progenitor cells and for identifying subpopulations thereof that are suitable for transplantation. The assay of the present invention is particularly useful for quality control and monitoring of the growth potential in the stem cell transplant setting and would provide improved control over the reconstitution phase of transplanted cells.

The present invention addresses the need for rapid assays that will determine the proliferative status of isolated hematopoietic stem and progenitor cells and of subpopulations of differentiated cells thereof.

One aspect of the present invention provides a high-throughput assay method useful for rapidly determining the proliferative status of a population of primitive hematopoietic cells as a function of the ATP content of the cells, the method comprising incubating a primitive hematopoietic cell population in a cell growth medium having a concentration of fetal bovine serum of between 0% and about 30%, a concentration of methyl cellulose between about 0.4% and about 0.7%, and in an atmosphere having less than about 7.5% oxygen. The cell population is contacted with a reagent capable of generating luminescence in the presence of ATP and the luminescence generated by the reagent is detected. The level of luminescence indicates the amount of ATP in the cell population, wherein the amount of ATP indicates the proliferative status of the primitive hematopoietic cells.

One embodiment of the method of the present invention further comprises the step of contacting the primitive hematopoietic cell population with at least one cytokine and optionally may further comprising the step of generating a cell population substantially enriched in hematopoietic stem cells.

In another embodiment of the method of the present invention, the cell population is substantially enriched in at least one hematopoietic progenitor cell lineage.

Another aspect of the present invention is a high-throughput assay method for rapidly identifying a population of primitive hematopoietic cells having a proliferative status suitable for transplantation into a patient. The method of the present invention, therefore, may comprise incubating a primitive hematopoietic cell population in a cell growth medium having a concentration of fetal bovine serum between 0% and about 30%, a concentration of methyl cellulose between about 0.4% and about 0.7%, and in an atmosphere having less than about 7.5% oxygen. The primitive hematopoietic cell population is contacted with at least one cytokine, typically before the incubation of the cells. Thereafter, the cell population is contacted with a reagent capable of generating luminescence in the presence of ATP. The luminescence thereby generated indicates the proliferative status of the primitive hematopoietic cells, which in turn indicates the suitability of the cell population for transplantation into a recipient patient.

Yet another aspect of the present invention is a high-throughput assay method for rapidly identifying a compound capable of modulating the proliferative status of a population of primitive hematopoietic cells. In this aspect of the present invention, a first target cell population comprising primitive hematopoietic cells is incubated in cell a growth medium having a concentration of fetal bovine serum between 0% and about 30%, a concentration of methyl cellulose between about 0.4% and about 0.7%, and in an atmosphere having less than about 7.5% oxygen. The method further comprises providing a plurality of second target primitive hematopoietic cell populations, contacting the first and second primitive hematopoietic cell populations with at least one cytokine before incubating the cell cultures, contacting the first and second target cell populations with at least one test compound, contacting the target cell populations with a reagent capable of generating luminescence in the presence of ATP. The luminescence generated is detected by the reagent contacting the target cell populations, the level of luminescence indicating the proliferative status of the primitive hematopoietic cells. The proliferative status of the plurality of the second target cell populations with the proliferative status of the first target population of primitive hematopoietic cells not in contact with the test compound, thereby identifying a test compound capable of modulating the proliferative status of a target cell population.

Additional objects and aspects of the present invention will become more apparent upon review of the detailed description set forth below when taken in conjunction with the accompanying figures, which are briefly described as follows.

BRIEF DESCRIPTION OF THE FIGURES

FIGS. 1A-4B illustrate the correlation between the initial plated cell concentration (0.25, 0.5, 0.75, 1, 1.5 $2 \times 10^5$/well) and the mean (FIGS. 1A, 2A, 3A and 4A respectively) or sum (FIGS. 1B, 2B, 3B, and 4B respectively) of relative luminescence units (RLU) measured at 4 days (FIGS. 1A and 1B), 7 days (FIGS. 2A and 2B), 10 days (FIGS. 3A and 3B) and 14 days (FIGS. 4A and 4B) after culture initiation, as a function of the integration time and/or gain of the plate reader. In FIGS. 1A-4B the value 2000 represents an integration time of 2000 ms. "Max" represents the maximum integration time. The values 200, 215, 225 or 250 represent the gains that were used with the respective integration times.

DETAILED DESCRIPTION OF THE PREFERRED EMBODIMENTS

Figure 1:
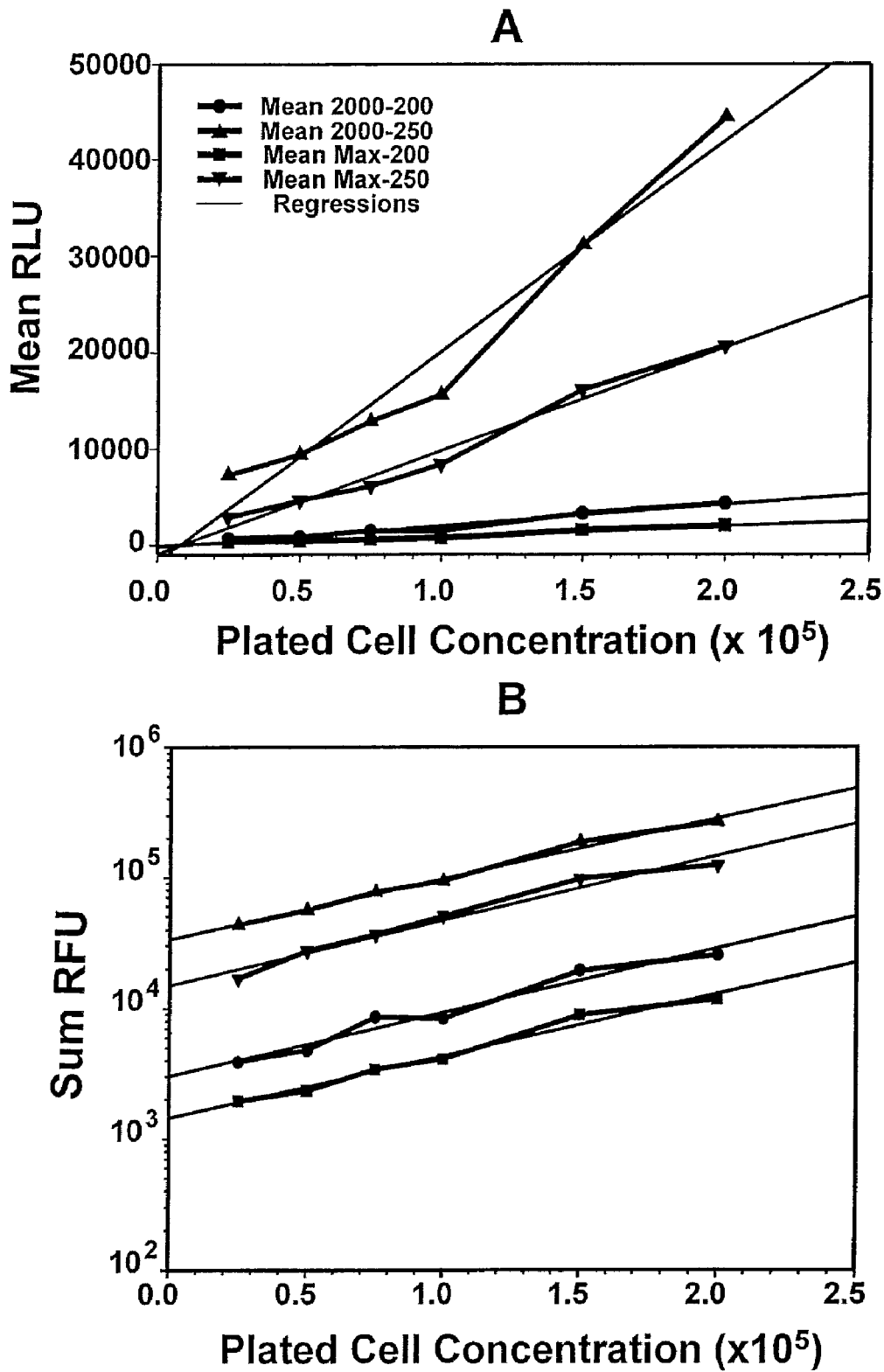
Figure 2:
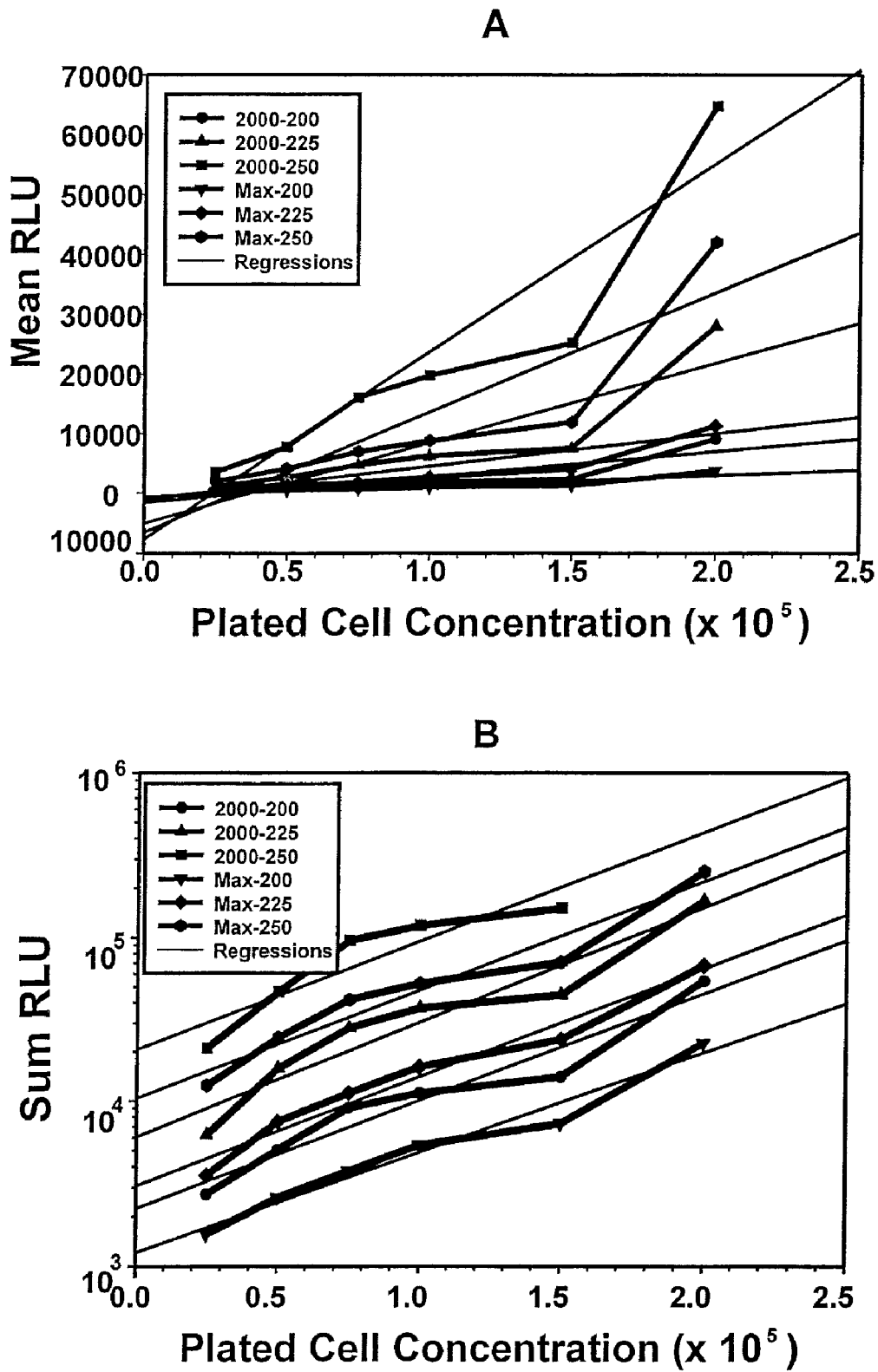
Figure 3:
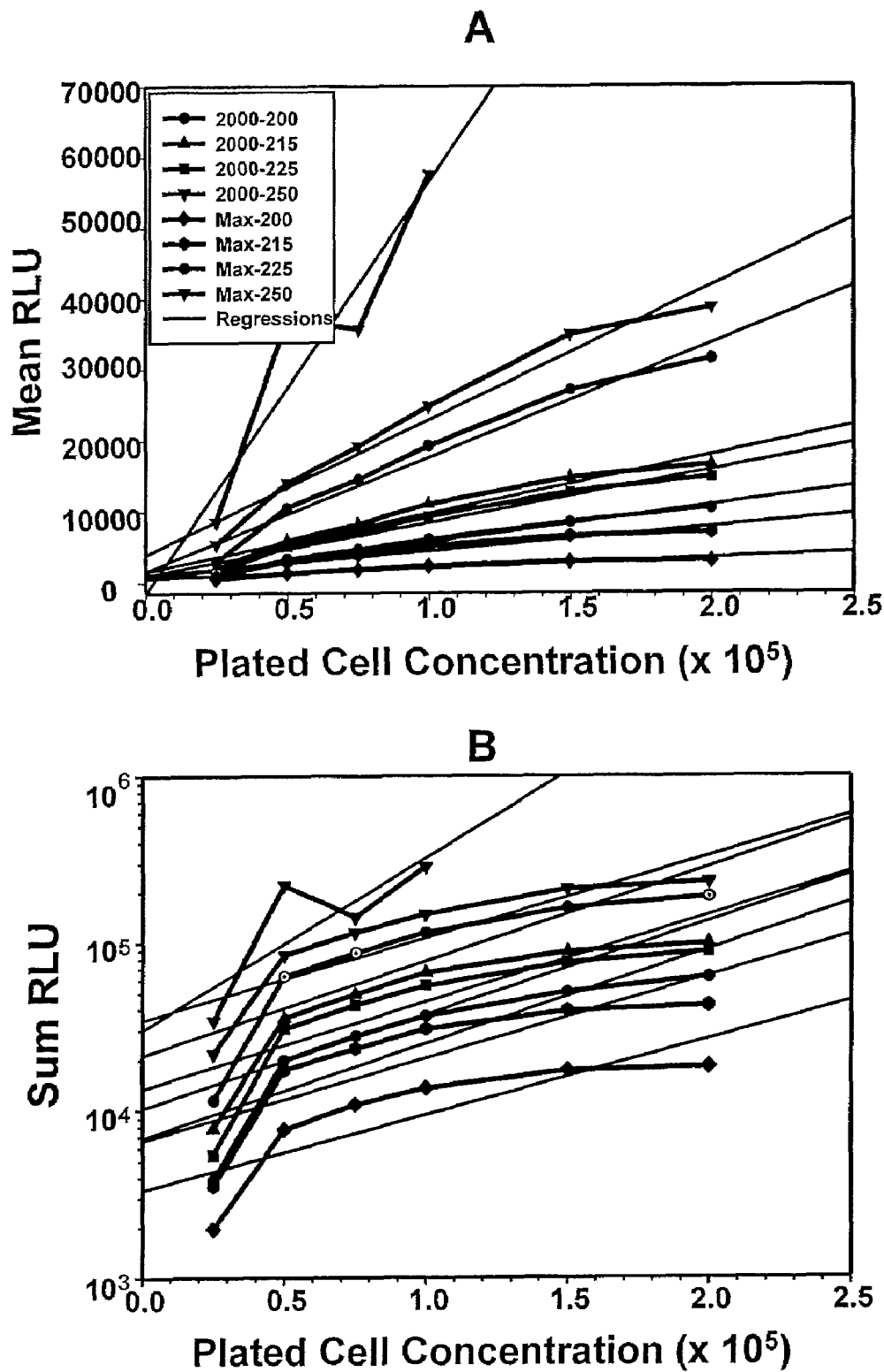
Figure 4:
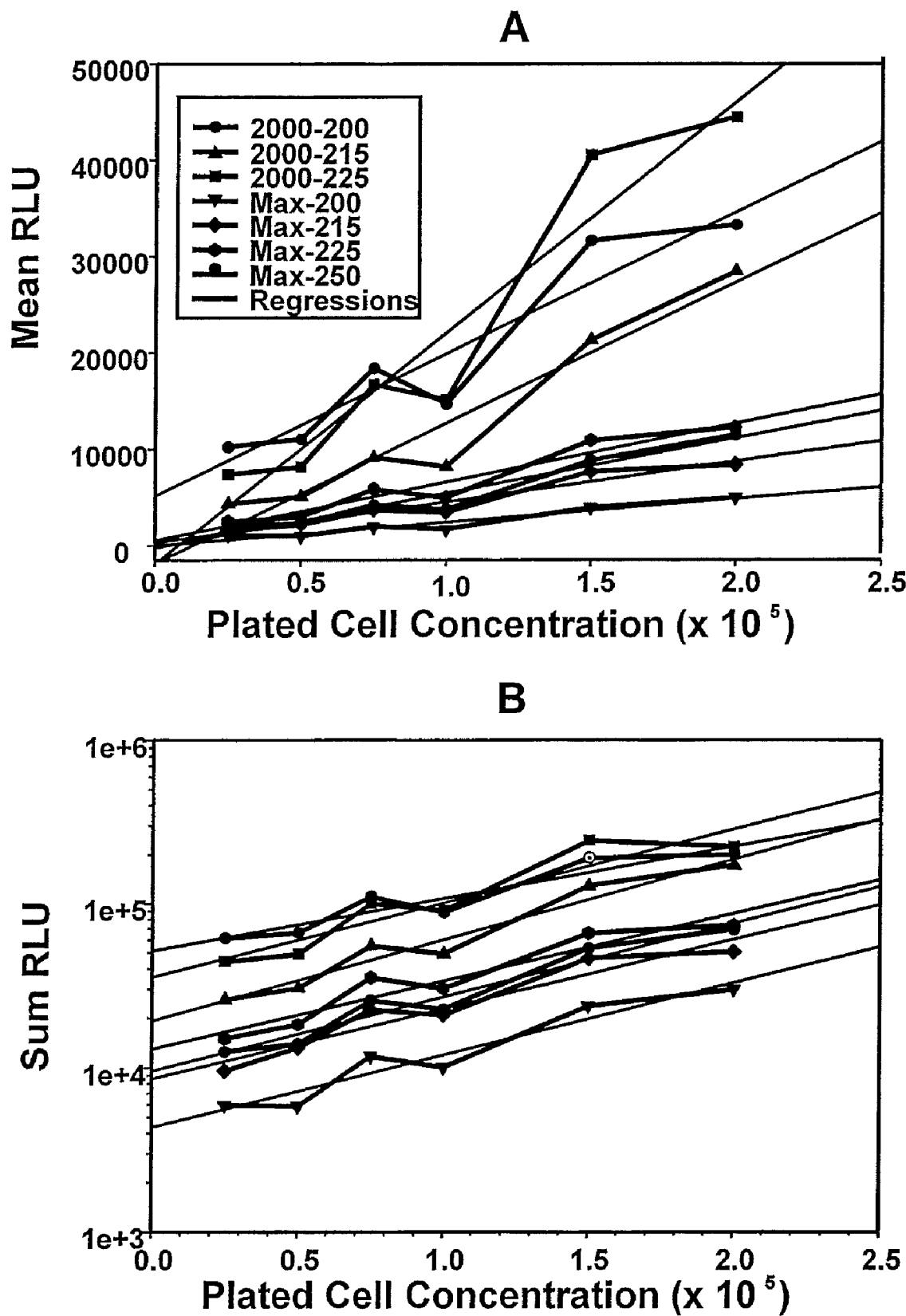

A full and enabling disclosure of the present invention, including the best mode known to the inventor of carrying out the invention, is set forth more particularly in the remainder of the specification, including reference to the Examples. This description is made for the purpose of illustrating the general principles of the invention and should not be taken in the limiting sense.

The methods of the present invention provides high-throughput assays for detecting and measuring the proliferative status of populations of primitive hematopoietic stem and progenitor cells, and cell lineages derived therefrom.

The methods of the present invention are especially useful when applied to populations of primitive hematopoietic cells including primary cells isolated from peripheral blood cells and bone marrow cells and hematopoietic stem and progenitor cells. The methods of the present invention, however, may be applied to any population of proliferating cells, including cells isolated from tissues and solid tumors.

The methods of the present invention can also be used to distinguish subpopulations of cells that may differ in the response to cytotoxic inhibitors, or activators such as cytokines The methods may be used to optimize the inhibitors to achieve maximum efficacy against a subpopulation of proliferating cells. An optimized dose, determined from an isolated small sample of the cell population of a patient, may be administered to the proliferating cells in vivo, wherein the optimized dose may be administered systemically to the human or animal patient having the proliferating subpopulation of cells, thereby reducing the likelihood of potentially harmful side-effects to the recipient patient.

The high-throughput assay methods of the present invention may also be used to determine the proliferative status of a population of hematopoietic stem or progenitor cells to determine their suitability and acceptability for transplantation into a recipient animal or human patient.

DEFINITIONS

The term "animal" as used herein refers to any vertebrate animal other than a human having a population of cells wherein at least one subpopulation of the cells may be proliferating or induced to proliferate. The term "animal" as used herein also refers to mammals including, but not limited to, bovine, ovine, porcine, equine, canine, feline species, non-human primates including apes and monkies, rodents such as rat and mouse, and lagomorphs such as rabbit and hare.

The term "tissue" as used herein refers to a group or collection of similar cells and their intercellular matrix that act together in the performance of a particular function. The primary tissues are epithelial, connective (including blood), skeletal, muscular, glandular and nervous.

The term "cell" or "cells" as used herein refers to any cell population of a solid or non-solid tissue including, but not limited to, a peripheral blood cell population, bone marrow cell population, a leukemic cell line population and a primary leukemic cell line population or a blood stem cell population. The cells may be hematopoietic cells, including bone marrow, umbilical cord blood, fetal liver cells, yolk sac and differentiating embryonic stem cells or differentiating primordial germ cells or embryonic germ cells. The cells may be a primary cell line population including, but not limited to, a leukemic cell line. Examples of leukemic cell lines include, but are not limited to, an acute lymphocytic leukemia, an acute myeloid leukemia, a chronic lymphocytic leukemia, a chronic myeloid leukemia and a pre-B acute lymphocytic leukemia. Such cell lines include, but are not limited to, acute myelogenous leukemia, acute T-cell leukemia, acute lymphoblastic leukemia, chronic myeloid leukemia, acute monocytic leukemia and B-cell leukemia. The term "target cell population" as used herein refers to any cell population, especially hematopoietic stem and progenitor cells, or subpopulations thereof, that may be contacted with a test compound, wherein the test compound may modulate the proliferation of the cells in a positive or a negative direction depending upon the compound and the target cell population.

The term "cell line" refers to cells that are harvested from a human or animal adult or fetal tissue, including blood and cultured in vitro, including primary cell lines, finite cell lines, continuous cell lines, and transformed cell lines.

The term "cell lineage" as used herein refers to a cell line derived from a progenitor or stem cell, including, but not limited to a hematopoietic stem or progenitor cell.

The term "cell cycle" as used herein refers to the cycle of stages in the replication of a eukaryotic cell. The cycle comprises the four stages G1, S, G2 and M, wherein the S phase is that portion of the cycle wherein the nucleic acid of the cell is replicated. Thus, a cell identified as being in the S-phase of the cell cycle is also identified as being a proliferating cell.

The term "proliferative status" as used herein refers to whether a population of hematopoietic stem or progenitor cells, or a subpopulation thereof, are dividing and thereby increasing in number, in the quiescent state, or whether the cells are not proliferating, dying or undergoing apoptosis.

The terms "modulating the proliferative status" or "modulating the proliferation" as used herein refers to the ability of a compound to alter the proliferation rate of a population of hematopoietic stem or progenitor cells A compound may be toxic wherein the proliferation of the cells is slowed or halted, or the proliferation may be enhanced such as, for example, by the addition to the cells of a cytokine or growth factor.

The term "quiescent" refers to cells that are not actively proliferating by means of the mitotic cell cycle. Quiescent cells (which include cells in which quiescence has been induced as well as those cells which are naturally quiescent, such as certain fully differentiated cells) are generally regarded as not being in any of the four phases G1, S, G2 and M of the cell cycle; they are usually described as being in a G0 state, so as to indicate that they would not normally progress through the cycle. Cultured cells can be induced to enter the quiescent state by various methods including chemical treatments, nutrient deprivation, growth inhibition or manipulation of gene expression, and induced to exit therefrom by contacting the cells with cytokines or growth factors.

The term "primary cell" refers to cells obtained directly from a human or animal adult or fetal tissue, including blood. The "primary cells" or "cell lines" may also be derived from a solid tumor or tissue, that may or may not include a hematopoietic cell population, and can be suspended in a support medium. The primary cells may comprise a primary cell line.

The term "primitive hematopoietic cell" as used herein refers to any stem, progenitor or precursor cell that may be induced to differentiate and/or proliferate to form a population of hematopoietic cells.

The term "hematopoietic stem cells" as used herein refers to pluripotent stem cells or lymphoid or myeloid stem cells that, upon exposure to an appropriate cytokine or plurality of cytokines, may either differentiate into a progenitor cell of a lymphoid or myeloid cell lineage or proliferate as a stem cell population without further differentiation having been initiated. "Hematopoietic stem cells" include, but are not limited to, colony-forming cell-blast (CFC-blast), high proliferative potential colony forming cell (HPP-CFC) and colony-forming unit-granulocyte, erythroid, macrophage, megakaryocyte (CFU-GEMM) cells.

The terms "progenitor" and "progenitor cell" as used herein refer to primitive hematopoietic cells that have differentiated to a developmental stage that, when the cells are further exposed to a cytokine or a group of cytokines, will differentiate further to a hematopoietic cell lineage. "Progenitors" and "progenitor cells" as used herein also include "precursor" cells that are derived from some types of progenitor cells and are the immediate precursor cells of some mature differentiated hematopoietic cells. The terms "progenitor", and "progenitor cell" as used herein include, but are not limited to, granulocyte-macrophage colony-forming cell (GM-CFC), megakaryocyte colony-forming cell (CFC-mega), burst-forming unit erythroid (BFU-E), colony-forming cell-megakaryocyte (CFC-Mega), B cell colony-forming cell (B-CFC) and T cell colony-forming cell (T-CFC). Precursor cells" include, but are not limited to, colony-forming unit-erythroid (CFU-E), granulocyte colony forming cell (G-CFC), colony-forming cell-basophil (CFC-Bas), colony-forming cell-eosinophil (CFC-Eo) and macrophage colony-forming cell (M-CFC) cells.

The term "cytokine" as used herein refers to any cytokine or growth factor that can induce the differentiation of a hematopoietic stem cell to a hematopoietic progenitor or precursor cell and/or induce the proliferation thereof. Suitable cytokines for use in the present invention include, but are not limited to, erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin. The term "cytokine" as used herein further refers to any natural cytokine or growth factor as isolated from an animal or human tissue, and any fragment or derivative thereof that retains biological activity of the original parent cytokine. The cytokine or growth factor may further be a recombinant cytokine or a growth factor such as, for example, recombinant insulin. The term "cytokine" as used herein further includes species-specific cytokines that while belonging to a structurally and functionally related group of cytokines, will have biological activity restricted to one animal species or group of taxonomically related species, or have reduced biological effect in other species.

The terms "cell surface antigen" and "cell surface marker" as used herein may be any antigenic structure on the surface of a cell. The cell surface antigen may be, but is not limited to, a tumor associated antigen, a growth factor receptor, a viral-encoded surface-expressed antigen, an antigen encoded by an oncogene product, a surface epitope, a membrane protein which mediates a classical or atypical multi-drug resistance, an antigen which mediates a tumorigenic phenotype, an antigen which mediates a metastatic phenotype, an antigen which suppresses a tumorigenic phenotype, an antigen which suppresses a metastatic phenotype, an antigen which is recognized by a specific immunological effector cell such as a T-cell, and an antigen that is recognized by a non-specific immunological effector cell such as a macrophage cell or a natural killer cell. Examples of "cell surface antigens" within the scope of the present invention include, but are not limited to, CD3, CD4, CD8, CD34, CD90 (Thy-1) antigen, CD117, CD38, CD56, CD61, CD41, glycophorin A and HLA-DR, AC133 defining a subset of $CD34^+$ cells, CD19, and HLA-DR. Cell surface molecules may also include carbohydrates, proteins, lipoproteins or any other molecules or combinations thereof, that may be detected by selectively binding to a ligand or labeled molecule and by methods such as, but not limited to, flow cytometry.

The term "cell surface indicator" as used herein refers to a compound or a plurality of compounds that will bind to a cell surface antigen directly or indirectly, and thereby selectively indicate the presence of the cell surface antigen. Suitable "cell surface indicators" include, but are not limited to, cell surface antigen-specific monoclonal or polyclonal antibodies, or derivatives or combinations thereof, and which may be directly or indirectly linked to a signaling moiety. The "cell surface indicator" may be a ligand that can bind to the cell surface antigen, wherein the ligand may be a protein, peptide, carbohydrate, lipid or nucleic acid that is directly or indirectly linked to a signaling moiety.

The term "flow cytometer" as used herein refers to any device that will irradiate a particle suspended in a fluid medium with light at a first wavelength, and is capable of detecting a light at the same or a different wavelength, wherein the detected light indicates the presence of a cell or an indicator thereon. The "flow cytometer" may be coupled to a cell sorter that is capable of isolating the particle or cell from other particles or cells not emitting the second light.

The term "reagent capable of generating luminescence in the presence of ATP" as used herein refers to a single reagent or combination of components that, in the presence of ATP, will generate luminescence. The amount of luminescence may be reliably related to the amount of ATP present. An example of a reagent suitable for use in the present invention is the combination of luciferin and luciferase as described by Crouch et al. (*J. Immunol. Meth.* 160, 81-88 (2000)) and Bradbury et al. (*J. Immunol. Meth.* 240, 79-92 (2000)) incorporated herein by reference in their entireties.

The term "toxicity" as used herein refers to the ability of a compound or a combination of compounds to negatively modulate the proliferation of a population of hematopoietic stem or progenitor cells. It will be understood that the toxicity of a compound or compounds may be effective against one hematopoietic cell lineage and not against another, and may further include the ability of a compound to modulate the differentiation of a hematopoietic stem or progenitor cell.

The term "differentially distinguishable" as used herein refers to hematopoietic stem and progenitor cells, or any other animal cell, the proliferation status of which may be usefully determined by the assay methods of the present invention and which can be characterized into subpopulations based on, for example, different complements of cell surface markers.

Following longstanding law convention, the terms "a" and "an" as used herein, including the claims, are understood to mean "one" or "more".

Abbreviations

Abbreviations used in the present specification include the following: IL, interleukin; PBMC, peripheral blood mononuclear cells; PBS, phosphate-buffered saline (10 mM phosphate, 138 mM NaCl, 2.7 mM KCl, pH 7.4); FBS, fetal bovine serum; BSA, bovine serum albumen Reference now will be made in detail to the aspects and embodiments of the invention. Each example is provided by way of explanation of the invention, and not a limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

The high-throughput assay methods of the present invention comprise the detection and enumeration of a population of hematopoietic cells by measuring the metabolic activity of samples of proliferating cells as indicated by their ATP content. The ATP content can be measured by detecting the luminescence generated by a ATP-dependent reaction requiring, for example, contacting the cells with an ATP-releasing agent and an ATP-monitoring agent. A suitable system for detecting ATP by the emission of luminescence comprises the combination of luciferin and luciferase, although it is contemplated that any method that will emit a detectable signal, the intensity of which may be correlated to the amount of ATP in a cell culture may be within the scope of the present invention.

The high-throughput assay method of the present invention allows for the detection of actively proliferating subpopulations of hematopoietic stem and progenitor cell lineages that have been induced to undergo proliferation by exposure of the cell population to one or more cytokines. Most hematopoietic cell lineages can be induced to proliferate by contacting the cell population with at least one cytokine. It is, therefore, contemplated that a cytokine, or combination of cytokines, may be selected to induce the proliferation of a selected cell lineage. It is further contemplated to be within the scope of the assay methods of the present invention for a plurality of primitive hematopoietic stem or progenitor cell populations to be contacted with a plurality of cytokines or combinations of cytokines, thereby establishing populations of different proliferating cell lineages. The various proliferating cell lineages may then be used as target cells and contacted with one or more test compounds. The cell proliferation modulating activities, including toxicity, of the compounds or combinations and/or doses thereof may be compared and contrasted, as well as how the various cell lineages will react to the test compounds.

High-Throughput Assays of Hematopoietic Stem and Progenitor Cell Proliferation

Primitive hematopoietic cells can be isolated from suitable animal or human tissues including, for example, peripheral blood, bone marrow, or umbilical cord blood. Mononuclear cells, for example peripheral blood mononuclear cells (PBMCs) may be further isolated by methods such as density-gradient centrifugation. It is contemplated to be within the scope of the present invention for the primitive cell population to be further subdivided into isolated subpopulations of cells that are characterized by specific cell surface markers. The methods of the present invention may further include the separation of cell subpopulations by methods such as high-speed high-speed cell sorting, typically coupled with flow cytometry.

For example, the channels of a flow-cytometer and high-speed cell sorter could be set at 530 nm, typically used for FITC labeling, 670 nm used for APC labeling, and a UV channel, for Hoechst (Ho) 33342 or DAPI staining. Fluorescent compensation software such as the System II or Expo 32 (Beckman Coulter) can allow full use of all of these channels. Cell subpopulations can be selected based on the presence or absence of cell membrane antigen markers, the intracellular pH, and the cell cycle status. Exemplary methods for selectively distinguishing subpopulations of hematopoietic cells are described, for example, in PCT application Serial No: 20010012620, incorporated herein in by reference in its entirety.

Multiparameter analysis may be conducted on primary normal and leukemic samples or leukemic cell lines. The methods of the present invention, however, may be applied or adapted to any non-leukemic hematopoietic stem or progenitor cell population that might include a subpopulation of proliferating cells. An antigen indicator conjugated to APC can be used to selectively detect a normal blood stem cell subpopulation. Aliquots of cells may be labeled with panels comprising more than one biomarker. An example of one such panel incorporates CD38-FITC, CD34-APC, SNARF and Ho33342. Other examples of possible panels can include substituting CD38-FITC with CD117 (c-kit)-FITC, with CD91 (Thy-1)-FITC or with AC133-FITC.

The procedures of the present invention, therefore, can provide techniques to analyze combinations of cell markers as described above, or those specific for other lympho-hematopoietic lineages to differentiate the effects of inhibitors on normal different cell subpopulations. A similar reasoning can be applied to leukemic cell populations that also show aberrant flow cytometric profiles distinguishable from the normal population. A typical example would be chronic myeloid leukemia in chronic phase. However, in the case of ALL, the leukemic cell population can be defined by a high proportion of $CD19^+$ cells. Therefore, CD19 is a biomarker that can be used to differentiate between leukemic and non-leukemic populations. The selected cell subpopulations can then be applied to the high-throughput assays of the present invention, as described in Examples 1 and 2 below.

Cell surface indicators may be contacted with the hematopoietic stem or progenitor cells or leukemic cells thereof and the various subpopulations may be selectively separated by techniques such as flow cytometry or by attaching the cell surface indicators directly or indirectly to a separable solid support such as magnetic beads. The beads and the attached cells thereon can be isolated by a magnetic field.

In the methods of the present invention as described, for example, in Examples 1 and 2 below, target hematopoietic stem and/or progenitor cells are isolated from animal or human tissues and suspended at cell concentrations ranging from about $1-5 \times 10^2$ to about $1-2 \times 10^5$/ml. Since typical assay volumes are 100 µl, actual cell concentrations in the assay test vessels will be diluted to 1/10 of the original starting cell concentration. The cells are mixed and suspended in methyl cellulose containing 0% to about 30% concentration of fetal bovine serum (FBS), 1% detoxified bovine serum albumin (BSA), iron-saturated human transferrin at a final concentration of $1 \times 10^{-10}$ mol/L, α-thioglycerol at a final concentration of $1 \times 10^{-4}$ mol/L and cytokines/growth factors. The methyl cellulose concentration in the assays of the present invention is between about 0.4% and about 0.7%, with a preferred concentration for most cell populations of about 0.7%. One exemplary medium is Iscove's Modified Dulbecco's Medium (IMDM, Life Technologies, Rockville, Md.) although other suitable media capable of supporting the growth of hematopoietic cells may also be used. Low fetal bovine serum concentrations of between 0% and 10% can also be used. When the assay methods of the present invention are used under serum-free conditions, insulin (10 µg/ml) and, where necessary, low density lipoproteins (40 µg/ml) can replace the FBS.

A stock cell culture is aliquoted into sample chambers. While sample chambers may be the wells of a multi-well tissue culture plate, such as a 48- or 96-well plate, it is also contemplated to be within the scope of the present invention to conduct the assays of the present invention in any other suitable reaction vessels including, but not limited to, individual tubes, wells of plates and the like. Culture plates with a well surface area of about 35 mm$^2$ and a low ring of about 2 mm high are especially useful and allow colonies to be counted that are against the wall of the ring. Preferably the sample chambers are not tissue culture treated. For luminescence assays to be performed, multi-well plates that reduce background light emission or scatter when the plates are being enumerated in the plate reader may also be used. While it is desirable to use replicate reactions, it is to be understood that a single reaction sample may be used for determining the proliferative status of cells for each data point. However, replicate reactions are to be preferred wherever an increase in accuracy is necessary. For example, reactions may be replicated once, twice or more times, including on a single multi-well plate, although quadruple reactions are preferred.

The assay methods of the present invention especially contemplate that the cultures can be incubated in a humidified atmosphere having a low oxygen tension for a period preferably extending to about 10 days but also to at least about 14 days. A suitable oxygen concentration range is from about 3.5% oxygen to about 7.5% oxygen, most preferably about 5.0% oxygen, and further comprising about 5% $CO_2$ as described by Bradley et al. (*J. Cell Physiol.* 97, 517-522 (1968) and Rich & Kubanek (*Exp. Hemat.* 52, 579-588 (1982) incorporated herein by reference in their entireties.

Regardless of the instrument parameters used, there is a direct correlation between the cell concentration plated in the wells and the mean, or sum, of the relative luminescence units obtained. To avoid large standard deviations, an integration time of 1000 ms may be used, although other integration times may usefully be selected.

The high-throughput assay method of the present invention further includes contacting a hematopoietic stem or progenitor cell population with at least one cytokine that can induce the proliferation of the stem or progenitor cell population. It is contemplated that the cytokine of a combination of cytokines may be selected to induce the differentiation and proliferation of selected subpopulations of hematopoietic cell lineages. Exemplary cytokines include, but are not limited to erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor. Additional growth factors may also be included to boost the proliferative status of a particular culture of cells including such factors as insulin-like growth factor, insulin and recombinant insulin. Examples of cytokines or combinations thereof that may be used in the assay methods of the present invention and the specific targeted stem, progenitor or precursor cell types, and the resulting expanded cell lineages are given in Example 3 and Table 1 below.

High-Throughput Assay Methods for Toxicity Testing with Hematopoietic Stem and Progenitor Cells It is further contemplated that a cell lineage that is induced to proliferate by contacting a first primitive hematopoietic stem or progenitor cell population with a cytokine or combination of cytokines may further be contacted with a test compound that may have a cytotoxic effect or a cell proliferation enhancing effect. The degree of modulation of cell proliferation or differentiation may also be determined by comparing the proliferation of the cell lineage in the presence of the test compound, and in its absence from the culture of a second targeted cell population or plurality of second cell populations. It is within the scope of the assay methods of the present invention for a plurality of test compounds to be compared for their cytotoxic effects on one, or a plurality, of proliferating target cell lineages. To these ends, a plurality of hematopoietic stem or progenitor cell populations may, for example, be plated in the wells of a multi-well plate or in individual chambers, thereby allowing rapid testing of multiple samples.

It is also contemplated that the high-throughput assays of the present invention may be used to determine the ability of a test compound to increase the proliferation of a population of hematopoietic stem or progenitor cells. Such proliferation enhancing compounds include, for example, cytokines and growth factors.

It is further contemplated that the assay methods of the present invention may be used with a range of concentrations of the test compound which may be contacted with a plurality of cell populations of the same cell lineage, whereupon the IC50 or the IC90 for the test compound acting against the targeted cell population or a subpopulation thereof may be calculated.

High-Throughput Assay Methods for Screening Hematopoietic Stem and Progenitor Cell Populations for Suitability for Transplantation The high-throughput assay methods of the present invention are also suitable for screening a population of hematopoietic stem or progenitor cells to determine the proliferation status of the cells or subpopulations thereof wherein the proliferative status will indicate the suitability of the stem or progenitor cells for transplantation into a recipient animal or human host. The high-throughput assay of the present invention will allow the selection of populations of primitive hematopoietic cell that will likely proliferate and maintain engrafment within the recipient patient.

By determining the sum or mean of the relative luminescence units (RLU) in all replicates of a single sample at a specified time point during the incubation procedure, for example at 4, 7, 10 or 14 days of incubation, the assay can be used to rapidly and quantitatively determine: (a) the proliferative status of a hematopoietic stem or progenitor cell population or of cells of a specific progenitor and differentiation lineage and compare such in parallel assays; (b) if cells from a particular source exhibit a normal or abnormal proliferative capacity; and (c) whether a compound (e.g. growth factor, cytokine, drug, neutraceutical, environmental agent), will have a positive or negative effect of the proliferative status of the cells in a particular cell population. The assay, even of multiple samples, can be completed within 30 min, calculated from the time of adding the ATP releasing agent to the conclusion of the luminescence measurement.

The high-throughput stem/progenitor cell assay (HT-SPCA) of the present invention does not count colonies or differentiate between colony types. Rather, the HT-SPCA of the present invention measures the proliferation status of cells within the colonies by determining the amount of ATP being produced by the cells. With colony growth in the methyl cellulose assay system of the present invention, some cells in the cultures will begin to proliferate and form aggregates or clusters. However, the proliferative status of the cell population may be limited due to their late stage of differentiation. Thus, a small colony may ensue within a short incubation period, but cell proliferation will rapidly cease.

In the assay methods of the present invention, the culture conditions include α-thioglycerol to maintain molecules in a reduced form, and the cultures are incubated under low oxygen tension of between about 3.5% oxygen and about 7.5% oxygen, both conditions reducing oxygen toxicity. The cell aggregate or colony can be maintained in a stagnant or non-proliferative state for between about 2 and about 3 weeks. Other cells, however, that are developmentally more primitive, for example, stem and progenitor cells, have a greater proliferative capacity and will begin to form colonies after a certain lag period of time. These cells will continue to divide throughout the whole of the incubation period. Eventually, the proliferative capacity of the cells within these colonies will also decrease and finally cease.

This ability of the assay method of the present invention to distinguish primitive hematopoietic cells from more mature, differentiated lineages contrasts with the conventional manual assay methods. In the manual assay, in which colonies are counted under a microscope, proliferating cells cannot be readily distinguished from non-proliferating cells. The size of the colony, however, may indicate the "primitiveness" of the cell that gave rise to that colony. Thus, the larger the colony, the greater the possibility of the colony deriving from a more primitive cell. In the HT-SPCA method of the present invention, the size of the colony of the present invention, however, is irrelevant. Rather, it is the proliferative status of the cells within the colonies within the same well that is measured, as documented in Example 3 below.

One aspect of the present invention, therefore, is a high-throughput assay method for rapidly determining the proliferative status of a population of primitive hematopoietic cells, the method comprising the steps of providing a cell population comprising primitive hematopoietic cells, incubating the cell population in a cell growth medium comprising a concentration of fetal bovine serum between 0% and about 30% and a concentration of methyl cellulose between about 0.4% and about 0.7%, and in an atmosphere having between about 3.5% oxygen about 5.5% oxygen, preferably 5.0% oxygen, contacting the cell population with a reagent capable of generating luminescence in the presence of ATP, and detecting luminescence generated by the reagent contacting the cell population, the level of luminescence indicating the amount of ATP in the cell population, wherein the amount of ATP indicates the proliferative status of the primitive hematopoietic cells.

In one embodiment of the method of the present invention, the concentration of fetal bovine serum is between about 0% and 10%.

In another embodiment of the method of the present invention, the concentration of methyl cellulose is about 0.7%.

In yet another embodiment of the present invention, the concentration of oxygen in the atmosphere is about 5%.

Another embodiment of the method of the present invention further comprises the step of contacting the primitive hematopoietic cell population with at least one cytokine and optionally may further comprise the step of generating a cell population substantially enriched in hematopoietic stem cells.

One embodiment of the method of the present invention comprises the step of generating a cell population substantially enriched in at least one hematopoietic progenitor cell lineage.

In one embodiment of the method of the present invention, the primitive hematopoietic cells are hematopoietic stem cells.

In another embodiment of the method of the present invention, the primitive hematopoietic cells are hematopoietic progenitor cells.

In yet another embodiment of the method of the present invention, the population of primitive hematopoietic cells comprises hematopoietic stem cells and hematopoietic progenitor cells.

In still another embodiment of the method of the present invention, the primitive hematopoietic cells are primary hematopoietic cells.

In one embodiment of the method of the present invention, the primary hematopoietic cells are isolated from animal tissue selected from the group consisting of peripheral blood, bone marrow, umbilical cord blood, yolk sac, fetal liver and spleen.

In one embodiment of the method of the present invention, the animal tissue is obtained from a human.

In one embodiment of the method of the present invention, the animal tissue is selected from bone marrow, yolk sac, fetal liver and spleen.

In various embodiments of the method of the present invention, the animal is a mammal.

In various embodiments of the method of the present invention, the mammal is selected from the group consisting of cow, sheep, pig, horse, goat, dog, cat, non-human primates, rodents, rabbit and hare.

In another embodiment of the method of the present invention, the animal tissue is human tissue further selected from the group consisting of peripheral blood, bone marrow, umbilical cord blood fetal liver and spleen.

In yet another embodiment of the method of the present invention, the primary hematopoietic stem cells are isolated from peripheral blood.

Still another embodiment of the method of the present invention further comprises the step of selecting a differentially distinguishable subpopulation of primitive hematopoietic cells from the population of primitive hematopoietic cells, wherein the subpopulation of cells is defined by cell surface markers thereon.

In one embodiment of the method of the present invention, the step of selecting a differentially distinguishable subpopulation of primitive hematopoietic cells from the population of primitive hematopoietic cells comprises the steps of contacting the population of primitive hematopoietic cells with at least one cell surface marker indicator capable of selectively binding to a cell surface marker of a differentially distinguishable subpopulation of cells, and selectively isolating the at least one subpopulation of cells binding the at least one indicator.

In one embodiment of the method of the present invention, the cell surface marker is selected from the group consisting of CD3, CD4, CD8, CD34, CD90 (Thy-1) antigen, CD117, CD38, CD56, CD61, CD41, glycophorin A, HLA-DR, AC133 defining a subset of $CD34^+$ cells, CD19, and HLA-DR.

In one embodiment of the method of the present invention, the cell surface marker is $CD34^+$.

In one embodiment of the method of the present invention, the subpopulation of differentially distinguishable primitive cells is selectively isolated by magnetic bead separation.

In another embodiment of the method of the present invention, the subpopulation of differentially distinguishable primitive cells is selectively isolated by flow cytometry and cell sorting.

In yet another embodiment of the method of the present invention, the population of primitive hematopoietic cells comprises at least one stem cell lineage selected from the group consisting of colony-forming cell-blast (CFC-blast), high proliferative potential colony forming cell (HPP-CFC) colony-forming unit-granulocyte, erythroid, macrophage, megakaryocyte (CFU-GEMM).

In the various embodiments of the methods of the present invention, the population of primitive hematopoietic cells comprises at least one hematopoietic progenitor cell lineage selected from the group consisting of granulocyte-macrophage colony-forming cell (GM-CFC), megakaryocyte colony-forming cell (CFC-mega), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), colony-forming cell-megakaryocyte (CFC-Mega), B cell colony-forming cell (B-CFC) and T cell colony-forming cell (T-CFC).

Also, in the various embodiments of the methods of the present invention, the reagent capable of generating luminescence in the presence of ATP comprises luciferin and luciferase.

Also, in the various embodiments of the methods of the present invention, the at least one cytokine is selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin.

In one embodiment of the method of the present invention, the at least one cytokine is stem cell factor, interleukin-7 and Flt3L, and wherein the at least one cytokine generates a cell population substantially enriched in colony-forming cells blast (CFC-Blast) stem cells.

In another embodiment of the method of the present invention, the at least one cytokine is macrophage colony stimulating factor, interleukin-1, interleukin-3, interleukin-6 and stem cell factor, and wherein the at least one cytokine generates a cell population substantially enriched in hematopoietic high proliferative potential colony-forming cell (HPP-CFC) stem cells.

In yet another embodiment of the method of the present invention, the at least one cytokine is erythropoietin, granulocyte-macrophage colony stimulating factor, granulocyte colony stimulating factor, stem cell factor, interleukin-3, interleukin-6, and optionally Flt3L, and wherein the at least one cytokine generates a cell population substantially enriched in hematopoietic colony-forming cell erythroid, macrophage, megakaryocyte (CFC-GEMM) stem cells.

In still another embodiment of the method of the present invention, the at least one cytokine is selected from the group consisting of erythropoietin, erythropoietin and interleukin-3, erythropoietin and stem cell factor and erythropoietin, stem cell factor and interleukin-3, and wherein the at least one cytokine generates a cell population substantially enriched in the hematopoietic burst forming unit-erythroid (BFU-E) progenitor cells.

In still yet embodiment of the method of the present invention, the at least one cytokine is further selected from granulocyte-macrophage colony stimulating factor, granulocyte-macrophage colony stimulating factor and interleukin-3, and granulocyte-macrophage colony stimulating factor, interleukin-3 and stem cell factor, and wherein the at least one cytokine generates a cell population substantially enriched in hematopoietic granulocyte-macrophage colony-forming cell (GM-CFC) progenitor cells.

In another embodiment of the method of the present invention, the at least one cytokine is further selected from the groups consisting of thrombopoietin, and thrombopoietin, interleukin-3 and interleukin-6, and wherein the at least one cytokine generates a cell population substantially enriched in the hematopoietic megakaryocyte colony-forming cell (CFC-Mega) progenitor cells.

In yet another embodiment of the method of the present invention, the at least one cytokine is further selected from interleukin-2, and interleukin-7, Flt3L and interleukin-15, and wherein the at least one cytokine generates a cell population substantially enriched in the hematopoietic T cell colony forming cell (T-CFC) progenitor cells.

In still another embodiment of the method of the present invention, the at least one cytokine is selected from the group consisting of interleukin-7, and interleukin-7 and Flt3L, and wherein the at least one cytokine generates a cell population substantially enriched in the hematopoietic B cell colony-forming cell (B-CFC) progenitor cells.

In still yet another embodiment of the method of the present invention, the at least one cytokine is erythropoietin and wherein the at least one cytokine generates a cell population substantially enriched in the hematopoietic colony-forming unit-erythroid (CFU-E) progenitor cells.

In another embodiment of the method of the present invention, the at least one cytokine is selected from the group consisting of granulocyte-colony stimulating factor and granulocyte-macrophage colony stimulating factor, and wherein the at least one cytokine generates a cell population substantially enriched in the hematopoietic granulocyte colony-forming cell (G-CFC) progenitor cells.

In yet another embodiment of the method of the present invention, the at least one cytokine is selected from the group consisting of interleukin-3, and interleukin-3 and stem cell factor, and wherein the at least one cytokine generates a cell population substantially enriched in the hematopoietic colony-forming cell-Basophil (CFC-Bas) progenitor cells.

In still another embodiment of the method of the present invention, the at least one cytokine granulocyte-macrophage colony stimulating factor, interleukin-3 and interleukin-5, and wherein the at least one cytokine generates a cell population substantially enriched in the hematopoietic colony-forming cell-eosinophil (CFC-Eo) progenitor cells.

In still yet another embodiment of the method of the present invention, the at least one cytokine is selected from the group consisting of macrophage colony stimulating factor, macrophage colony stimulating factor and granulocyte-macrophage colony stimulating factor and interleukin-7, and granulocyte-macrophage colony stimulating factor, and wherein the at least one cytokine generates a cell population substantially enriched in the hematopoietic macrophage colony-forming cell (M-CFC) progenitor cells.

One embodiment of the method of the present invention further comprises the step of identifying a population of primitive hematopoietic cells having a proliferative status suitable for transplantation into a recipient patient.

Another embodiment of the method of the present invention further comprises the steps of providing a population of primitive hematopoietic cells comprising a target cell population, contacting the target cell population with a test compound, and determining the ability of the test compound to modulate the proliferative status of the target cell population.

In one embodiment of the method of the present invention, the population of primitive hematopoietic cells comprises a plurality of target cell populations, and the method further comprises the steps of contacting the plurality of target cell populations with at least one test compound, determining the ability of the at least one test compound to alter the proliferation of the target cell population by comparing the proliferative status of the plurality of target cell populations with the proliferative status of a target population of primitive hematopoietic cells not in contact with the test compound, and identifying the at least one test compound modulating the proliferative status of a target cell population.

Another aspect of the present invention, therefore, is a high-throughput assay method for rapidly identifying a population of primitive hematopoietic cells having a proliferative status suitable for transplantation into a patient, comprising the steps providing a cell population comprising primitive hematopoietic cells, incubating the cell population in cell a growth medium comprising between 0% and 30% fetal bovine serum and a concentration of methyl cellulose between about 0.4% and about 0.7%, and in an atmosphere having between about 3.5% and about 7.5% oxygen, contacting the primitive hematopoietic cell population with at least one cytokine selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin, contacting the cell population with a reagent capable of generating luminescence in the presence of ATP, and detecting luminescence generated by the reagent contacting the at least two cell populations, the level of luminescence indicating the proliferative status of the primitive hematopoietic cells, and wherein the proliferative status of the primitive hematopoietic cells indicates the suitability of the cell population for transplantation into a recipient patient.

In one embodiment of this aspect of the method of the present invention, contacting the population of primitive hematopoietic cells with at least one cytokines generates a cell population substantially enriched in a hematopoietic stem cell lineage.

In one embodiment of the method of the present invention, the hematopoietic stem cell lineage is selected from the group consisting of colony-forming cell-blast (CFC-blast), high proliferative potential colony forming cell (HPP-CFC) colony-forming unit-granulocyte, erythroid, macrophage, megakaryocyte (CFU-GEMM).

In another embodiment of this aspect of the method of the present invention, contacting the population of primitive hematopoietic cells with at least one cytokine generates a cell population substantially enriched in at least one hematopoietic progenitor cell lineage.

In the various embodiments of this aspect of the method of the present invention, the population of primitive hematopoietic cells comprises at least one hematopoietic progenitor cell lineage selected from the group consisting of granulocyte-macrophage colony-forming cell (GM-CFC), megakaryocyte colony-forming cell (CFC-mega), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), colony-forming cell-megakaryocyte (CFC-Mega), B cell colony-forming cell (B-CFC) and T cell colony-forming cell (T-CFC).

Yet another aspect of the present invention is a high-throughput assay method for rapidly identifying a compound capable of modulating the proliferative status of a population of primitive hematopoietic cells, comprising the steps of providing a first target cell population comprising primitive hematopoietic cells, incubating the cell population in cell a growth medium comprising between 0% and 30% fetal bovine serum and a concentration of methyl cellulose between about 0.4% and about 0.7%, and in an atmosphere having between about 3.5% and about 7.5% oxygen, providing a plurality of second target cell populations comprising primitive hematopoietic cells, contacting the first and second target primitive hematopoietic cell populations with at least one cytokine selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, and insulin, contacting the first and second target cell populations with at least one test compound, contacting the first and second target cell populations with a reagent capable of generating luminescence in the presence of ATP, detecting luminescence generated by the reagent contacting the first and second target cell populations, the level of luminescence indicating the proliferative status of the primitive hematopoietic cells, and comparing the proliferative status of the plurality of the second target cell populations with the proliferative status of the first target population of primitive hematopoietic cells not in contact with the test compound, thereby identifying a test compound capable of modulating the proliferative status of a target cell population.

In the various embodiments of this aspect of the method of the present invention, contacting the first and second target populations of primitive hematopoietic cells with at least one cytokine generates cell populations substantially enriched in hematopoietic stem cells.

In other embodiments of the methods of the present invention, the hematopoietic stem cells are selected from the group consisting of colony-forming cell-blast (CFC-blast), high proliferative potential colony forming cell (HPP-CFC) colony-forming unit-granulocyte, erythroid, macrophage, megakaryocyte (CFU-GEMM).

Also, in the various embodiments of this aspect of the method of the present invention, contacting the first and second target populations of primitive hematopoietic cells with at least one cytokine generates cell populations substantially enriched in at least one hematopoietic progenitor cell lineage.

In the various embodiments of this aspect of the method of the present invention, the at least one hematopoietic progenitor cell lineage selected from the group consisting of granulocyte-macrophage colony-forming cell (GM-CFC), megakaryocyte colony-forming cell (CFC-mega), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), colony-forming cell-megakaryocyte (CFC-Mega), B cell colony-forming cell (B-CFC) and T cell colony-forming cell (T-CFC).

One embodiment of the method of the present invention further comprises the steps of contacting a target cell population with at least two concentrations of a test compound, and calculating the IC50 of the test compound.

Another embodiment of the method of the present invention further comprises the steps of contacting a target cell population with at least two concentrations of a test compound and calculating the IC90 of the test compound.

The present invention is further illustrated by the following examples, which are provided by way of illustration and should not be construed as limiting. The contents of all references, published patents and patents cited throughout the present application are hereby incorporated by reference in their entirety.

Example 1

Preparation of Incubated Hematopoietic Stem or Progenitor Cells

Isolation of Mononuclear cells

Mononuclear cells (MNC) were prepared from human peripheral blood, bone marrow or umbilical cord blood by density gradient centrifugation on Ficoll-Paque Plus by diluting the cell suspension 1:1 with sterile PBS and transferring up to 30 ml to a 15-20 ml cushion of Ficoll. Centrifugation was at 400 g for 20 mins at room temperature. The supernatant was discarded and the cells were resuspended in 50 ml of sterile PBS and re-centrifuged at 200 g for 10 mins at room temperature. Thereafter, the supernatant was discarded and the cells were resuspended in IMDM to ensure a single cell suspension. A cell count was determined. If not used immediately, the cells were placed on ice or at 4° C.

Cells from peripheral blood mononucleocytes (MNCs) were prepared at a final concentration of $2 \times 10^6$ cells/ml. MNCs from bone marrow and umbilical cord blood were prepared at final concentrations of $0.5-1 \times 10^6$ and $0.5-1 \times 10^5$ respectively.

Bulk Reagent Solutions

The following components were mixed in sterile tubes, usually in the following order, so that the final total volume of the culture mixture was 600 µl or multiples thereof. The volume prepared depended on the number of replicate assays required. A "master mix" of 600 µl was sufficient for 4-5 replicates of 100 µl each. If volumes of the master mix greater than 600 µl were required, medium was added first followed by methyl cellulose. This mixture was then mixed on a vortex mixer. If large quantities of methyl cellulose were added first, it became difficult to mix the components adequately.

(a) Serum-Containing Cultures
- (i) Methyl cellulose (stock at 2.6% v/v), 160 µl, (final concentration, 0.7% v/v)
- (ii) Fetal bovine serum (FBS), 180 µl
- (iii) α thioglycerol, 6 µl at a final concentration of $1 \times 10^{-4}$ M
- (iv) Human or bovine iron-saturated transferrin, 6 µl, final concentration of $1 \times 10^{-10}$ g/ml
- (v) Growth factors, individually or in combination, were selected from the following: erythropoietin, 1-3 U/ml; granulocyte-macrophage colony stimulating actor, 10-20 ng/ml; granulocyte colony stimulating factor, 10-20 ng/ml; macrophage colony stimulating factor, 10-20 ng/ml; thrombopoietin, 50 ng/ml; stem cell factor, 50 ng/ml; interleukin-1, 10-20 ng/ml; interleukin-2, 2-10 ng/ml; interleukin-3, 20 ng/ml; interleukin-6, 20 ng/ml; interleukin-7, 10 ng/ml. The volume added depended upon the concentration of the cytokine/growth factor stock solution, but typically were not greater than 6-µl. All growth factors were diluted in IMDM containing either 5% FBS or 1% BSA
- (vi) Cells diluted in IMDM to the required final concentration as described above and added at 60 µl.
- (vii) IMDM added to give a final stock solution volume of 600 µl (or multiples thereof).

(b) Serum-Free Cultures.

For serum-free conditions, the fetal bovine serum of (ii) above was replaced by a mixture of bovine serum albumen, transferrin and insulin added as a preformed mixture (BIT 9500, Stem Cells Technologies, Vancouver).

Once the basic components were added, including the growth factors that were required for the specific cell type to be analyzed, the contents were vortexed to yield a homogenous mixture. The reaction mixes were left to stand for a few minutes before dispensing to the wells of a 96-well plate or other arrays of receptacles. When cultures were incubated for more than 7 days, the outer wells of a 96-well plate were filled with 100 µl of sterile water to ensure that the cultures did not desiccate, even when a humidified tissue culture incubator was used.

Using a 1 ml syringe with an 18 gauge 1.5" needle, or a repeater pipette with a syringe capable of dispensing aliquots of 100 µl, serum-containing, or a serum-free culture prepared as described above was withdrawn slowly and dispensed into each of the replicate wells of a 96-well plate while ensuring that little or none of the master mix touched the sides of the wells.

Sample Incubation

Once the samples had been dispensed into the wells, the 96-well plate was placed in a fully humidified tissue culture incubator at 37° C. The cells were incubated in a low oxygen tension atmosphere of 5% $CO_2$ and 5% oxygen (obtained by replacing the oxygen in the incubator with nitrogen gas). The incubation period depended on the cell population to be tested.

Example 2

Measurement of the ATP Content of Incubated Hematopoietic Stem or Progenitor Cells After the incubation time has elapsed, the reagents from the ViaLight HS™ kits (Lumitech) were prepared for use. If necessary, the number of cell clusters (aggregates) or colonies that had developed in the wells of the incubated 96-well plates could be counted under an inverted microscope to ensure that a correlation between the sum, or mean, of the ratio of clusters/colonies to the relative luminescence units (RLU) was obtained (see below).

All reagents were allowed to attain room temperature before use. The ATP monitoring reagent was reconstituted as described by the manufacturers by adding 10 ml of the supplied buffer to the lyophilized reagent and waiting 15 mins. Alternatively, 1 ml of the buffer was used to reconstitute the reagent and the latter was then aliquoted into 1.5 ml microtubes and frozen while protected from light. Aliquots were then thawed and diluted to 1 ml final volumes using the supplied buffer as needed. The ATP monitoring reagent was protected from light at all times.

The required quantity of ATP releasing reagent was transferred into the reagent trough and 100 µl aliquots were transferred, using a multi-tip pipette, to each row or column of wells of the 96-well plated previously incubated as described in Example 1 above. After dispensing the reagent to one row or column, the contents of the wells were mixed at least 4-5 times with the pipette, so that the reagents mixed well with the methyl cellulose master mixes. Addition of the reagents diluted the methyl cellulose and mixing ensured that the cells came into contact with the ATP releasing reagent. This step had to be performed in a similar manner for all wells.

Once the ATP releasing reagent had been dispensed into all of the wells containing incubated cultures, and mixed therein, the plates were typically incubated in the dark for 5 min, although the incubation could proceed for up to 30 min without loss of sensitivity.

The required amount of ATP monitoring reagent was transferred to a new, clean trough and 20 µl of the reagent pipetted into each of the wells while ensuring that the contents of each well was mixed thoroughly. The plates were immediately transferred to a plate reader and the luminescence measured using an integration time of 1000 ms.

Measurement was given as relative luminescence units (RLU). In addition, since no two makes of luminescence readers are the same, the gain required to obtain sufficient RLU by each machine had to be empirically determined, but could also be standardized between machines as follows:

If space allowed on the same plate as the wells containing the incubated cell cultures, 100 µl of a $10^{-6}$ M standard ATP diluted in IMDM from a $10^{-5}$ M ATP stock solution was added to each of 4-6 wells. 100 µl of ATP releasing agent was then added and incubated for the same period as had been used for the cell culture wells. 20 µl of ATP monitoring reagent was then added and the plate transferred to the plate reader and the luminescence measured at an integration time of 1000 ms. The gain was adjusted such that the luminescence from the ATP standard was approximately 20,000 RLU. By adjusting the gain of the machine to obtain this number of RLU, and then reading the remaining wells of the plate (containing the incubated cells), no overflow values occurred, thereby obviating the need for a second or multiple reading. In all cases, the luminescence was measured in the shortest possible time period possible, because the luminescence decreased rapidly with time.

The correlation between the initial plated cell concentration (0.25, 0.5, 0.75, 1, 1.5 $2 \times 10^5$/well) and the mean (FIGS. 1A, 2A, 3A and 4A respectively) or sum (FIGS. 1B, 2B, 3B, and 4B respectively) of relative luminescence units (RLU) measured at 4 days (FIGS. 1A and 1B), 7 days (FIGS. 2A and 2B), 10 days (FIGS. 3A and 3B) and 14 days (FIGS. 4A and 4B) after culture initiation, as a function of the integration time and/or gain of the plate reader. In FIGS. 1A-4B the value 2000 represents an integration time of 2000 ms. "Max" represents the maximum integration time. The values 200, 215, 225 or 250 represent the gains that were used with the respective integration times.

Example 3

Figure 5:
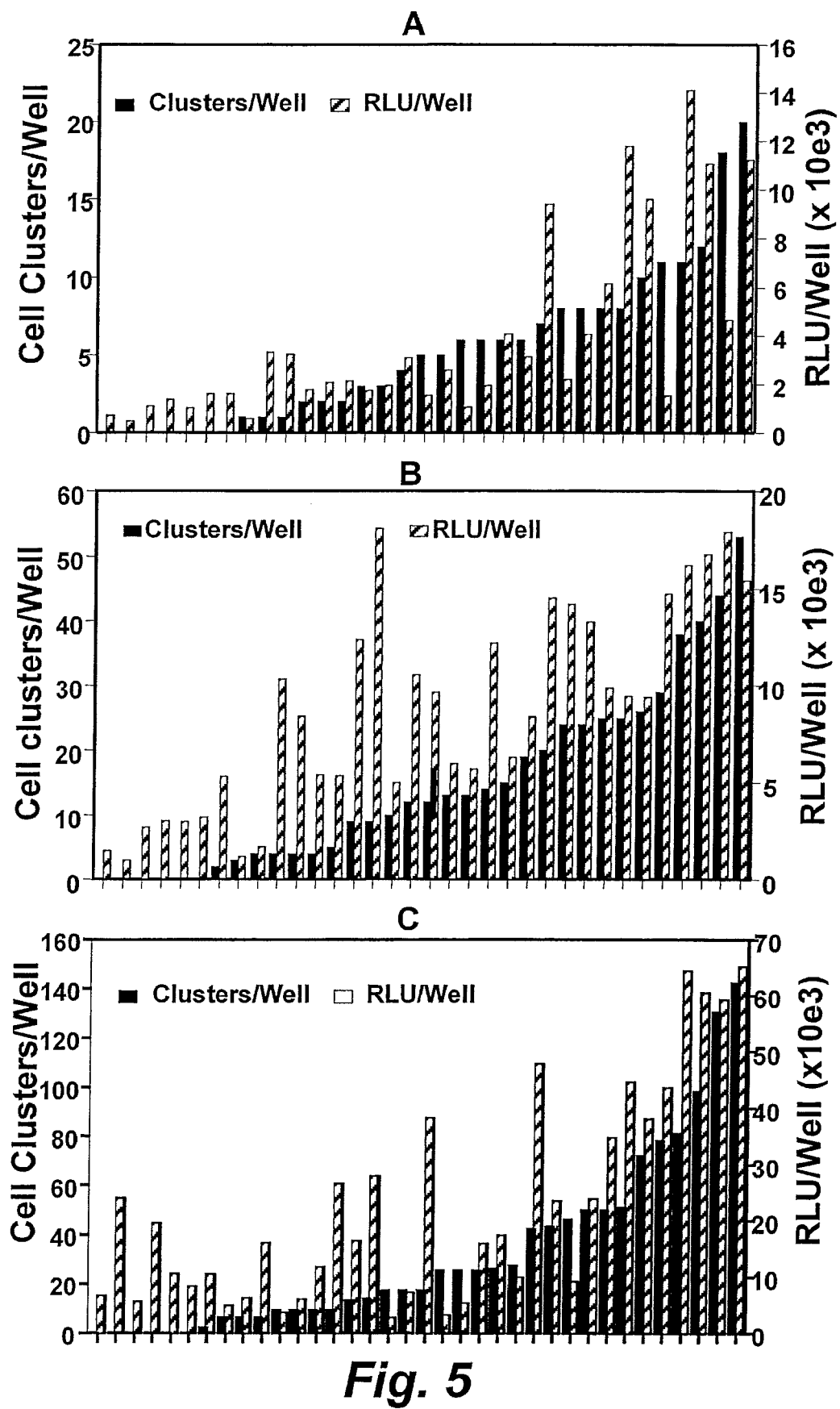
FIGS. 5A-5C illustrate histograms showing the number of cell clusters counted manually per well and the relative luminescence units (RLU) per well at day 7 (FIG. 5A), day 10 (FIG. 5B) and day 14 (FIG. 5C) of incubation.

Hematopoietic Stem and Progenitor Cell Lines and their Associated Cytokine Effectors Hematopoietic stem and progenitor cells are induced to differentiate into hematopoietic cell subpopulations by exposure to one or more growth factors/cytokines, as shown in Table 1 below.

were proliferating, while others were not, as shown in FIGS. 5A-5C. Wells, therefore, could contain few colonies, but still exhibit high cell proliferation. The results shown in FIGS. 5A-5C show that the number of cell clusters counted per well does not correlate with the cell proliferation as detected using the luminescence of the present invention.

In contrast, in those wells in which minimal or no cluster formation was detected, luminescence could be detected. In some wells, the luminescence was significantly greater than expected from the number of cell clusters counted, indicating that cell proliferation was occurring and that the proliferating cells, were primitive because of their increased proliferative capacity. On day 10, most wells contained cells that were proliferating. By day 14, this proliferative capacity was only

TABLE 1

| Development stage | Lineage | Population name | Population abbreviation | Stimulatory Growth factors and cytokines |
|---|---|---|---|---|
| Stem cell (Most primitive in vitro stem cell) | None | Long-term culture-initiating cells | LTC-IC | Stimulated by microenvironmental cells |
| Stem cell (Very primitive in vitro stem cell) | None | Colony-forming cell-Blast | CFC-Blast | Flt3L, SCF and IL-7 |
| Stem cell (Primitive in vitro stem cell) | None | High proliferative potential colony-forming cell | HPP-CFC | IL-1, IL-3, IL-6, SCF, M-CSF |
| Stem cell (Most mature in vitro stem cell) | None | Colony-forming cell granulocyte, erythroid macrophage, megakaryocyte | CFC-GEMM | IL-3, IL-6, GM-CFC, G-CSF, EPO, and SCF and/or Flt3L |
| Progenitor | Erythroid | Burst-forming unit-Erythroid | BFU-E | EPO<br>IL-3 and EPO<br>SCF and EPO<br>IL-3, SCF and EPO |
| Progenitor | Granulocyte-Macrophage | Granulocyte-macrophage colony-forming unit | GM-CFC | GM-CSF<br>IL-3 and GM-CSF<br>IL-3, SCF and GM-CSF |
| Progenitor | Megakaryocyte | Megakaryocyte colony-forming cell | CFC-Mega | TPO<br>IL-3, IL-6 and TPO |
| Progenitor | T lymphocyte | T cell colony-forming cell | T-CFC | IL-2<br>IL-7, Flt3L and IL-15 |
| Progenitor | B lymphocyte | B cell colony-forming cell | B-CFC | IL-7<br>IL-7 and Flt3L |
| Precursor | Erythroid | Colony-forming cell-erythroid | CFU-E | EPO |
| Precursor | Myeloid - Neutrohil | Granulocyte colony-forming cell | G-CFC | G-CSF<br>GM-CSF, high concentrations |
| Precursor | Myeloid - Basophil | Colony-forming cell-basophil | CFC-Bas | IL-3<br>IL-3 and SCF |
| Precursor | Myeloid - Eosinophil | Colony-forming cells-eosinophil | CFC-Eo | GM-CSF and IL-5 and IL-3 |
| Precursor | Macrophage | Macrophage colony-forming cell | M-CFC | M-CSF<br>M-CSF, GM-CSF, IL-3<br>GM-CSF, low concentrations |

Example 4

Proliferation of Hematopoietic Stem and Progenitor Cells Measured by Colony Counting and ATP Determination When cell proliferation was measured as a function of time in culture, some aggregates or colonies contained cells that seen in some wells, indicating that proliferation has ceased (RLU lower than the cell cluster count) or is declining. Those wells exhibiting a significantly greater RLU than determined by manual cell cluster counting showed that cells were present that were capable of extensive proliferation and were probably stem cells.

Little or no correlation existed between the number of individual colonies and the luminescence, as shown in FIGS.

6A-6C. However, under the typical incubation and culture conditions of the assay of the present invention, a well containing a few colonies, but with high indicated cell proliferation, showed that the cells in the culture have high proliferative capacity. In other words, the cells were primitive in nature.

Figure 6:
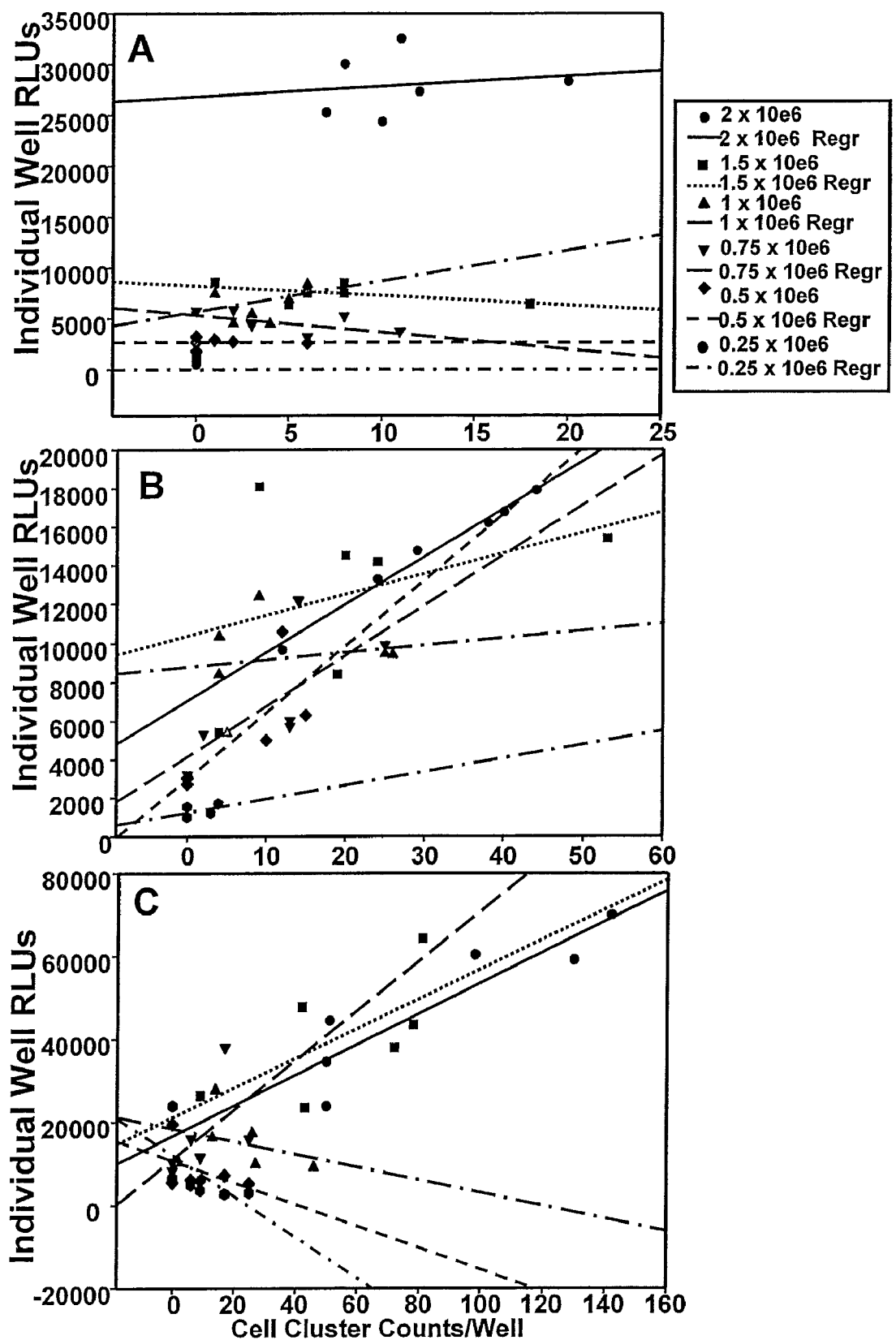
FIGS. 6A-6C graphically illustrate the lack of correlation between cell cluster counts per well and the relative luminescence units (RLU) per well on day 7 (FIG. 6A), day 10 (FIG. 6B) and day 14 (FIG. 6C) of culture incubation.
Figure 7:
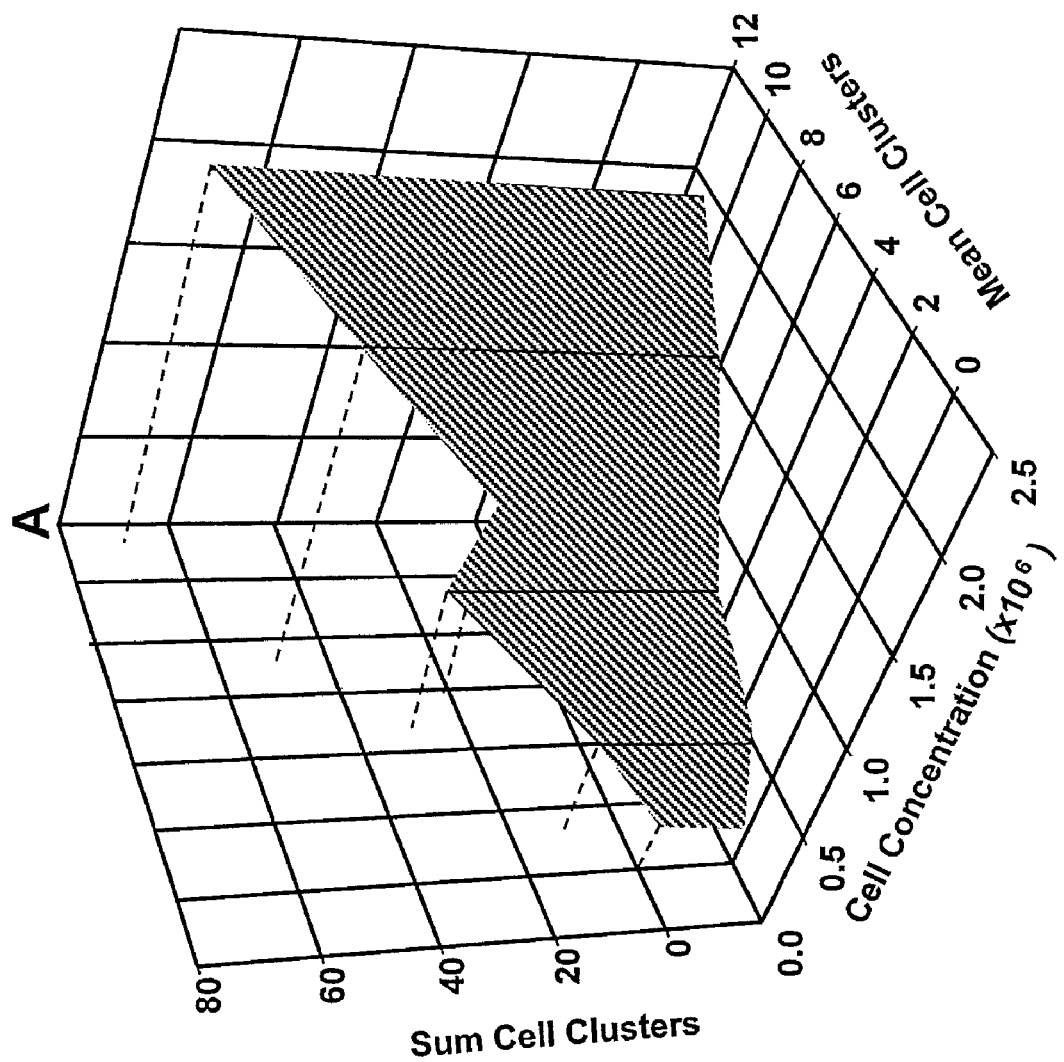
FIGS. 7A-7C show the direct correlation between the sum, or mean, of the cell cluster counts with the sum or mean of the relative luminescence units (RLU) measured on day 7 (FIG. 7A), day 10 (FIG. 7B) and day 14 (FIG. 7C) of culture incubation.
Figure 7:
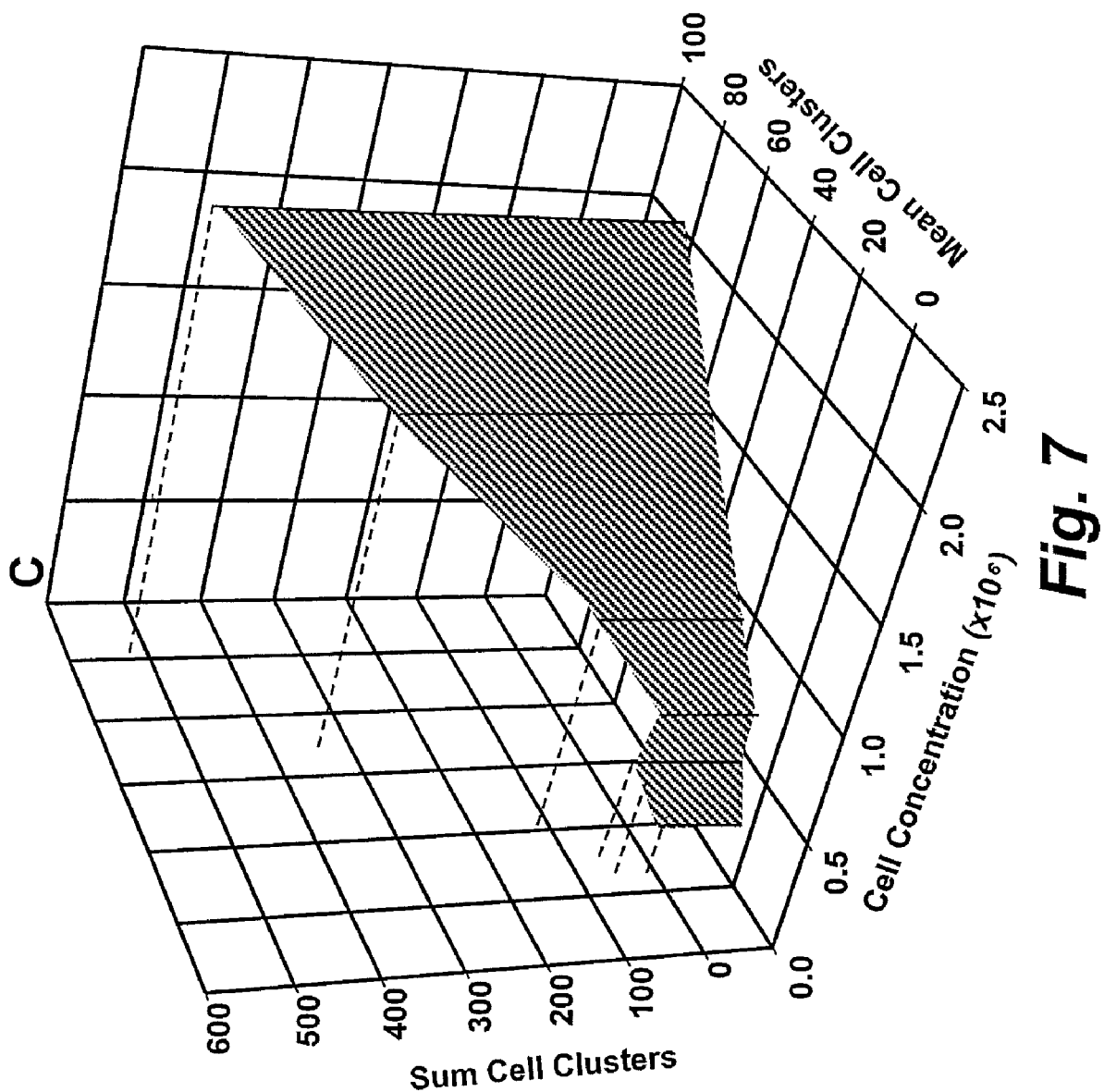

The number of colonies in a well did not generally correlate with the RLU from that well, as shown in FIGS. 6A-6C. In contrast, however, in the high-throughput assay method of the present invention, the luminescence measurements were made over the whole area of each and every replicate well, and not from the individual cell aggregates or colonies within these areas. The sum of the luminescent values of aggregates or colonies, or the mean of the aggregates or colonies from all replicate wells, can be predicted to correlate with the sum or mean of the luminescence emitted from the replicate wells, as shown in FIGS. 7A-7C.

Figure 8:
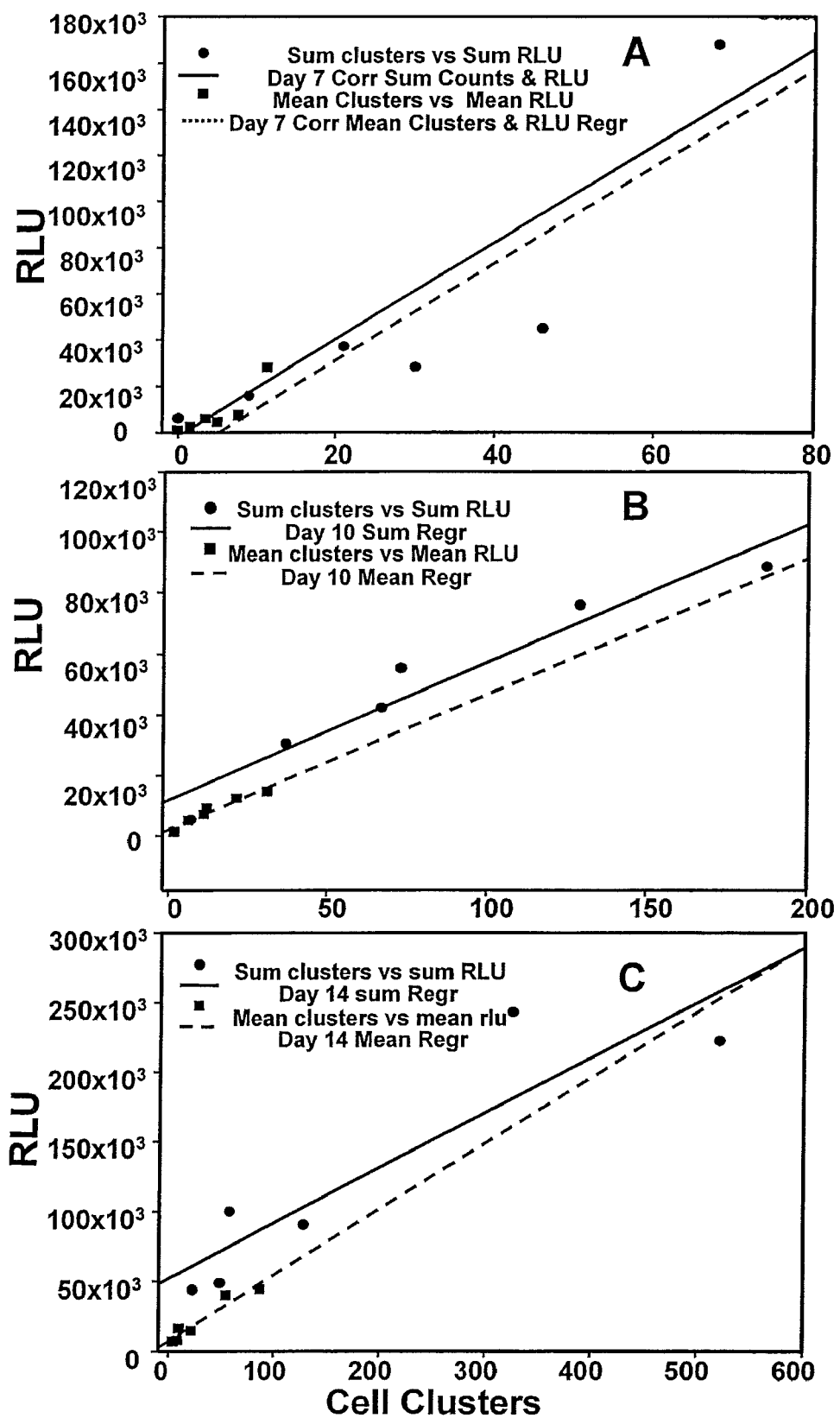
FIGS. 8A-8C show the correlation between cell concentration, sum of the replicate cell clusters and mean of the replicate cell clusters on day 7 (FIG. 8A), day 10 (FIG. 8B) and day 14 (FIG. 8C) of culture incubation.

There was a direct correlation between the sum, or mean, of all the cell aggregates or colonies from all replicate wells and the sum or mean of the RLU from all replicate wells. Furthermore, this relationship was cell dose dependent, as illustrated in FIGS. 8A-8C.

These results, as opposed to those in FIGS. 6A-6C indicate that using the sum or the mean of the replicates from particular sample, in this case, replicates at different cell concentrations, a direct correlation exists between the 3 parameters. If measurement of luminescence is depicted as the sum or the mean of the replicates, there was also be a direct correlation with the sum and/or mean of the cell clusters, as shown in FIGS. 8A-8D.

Figure 9:
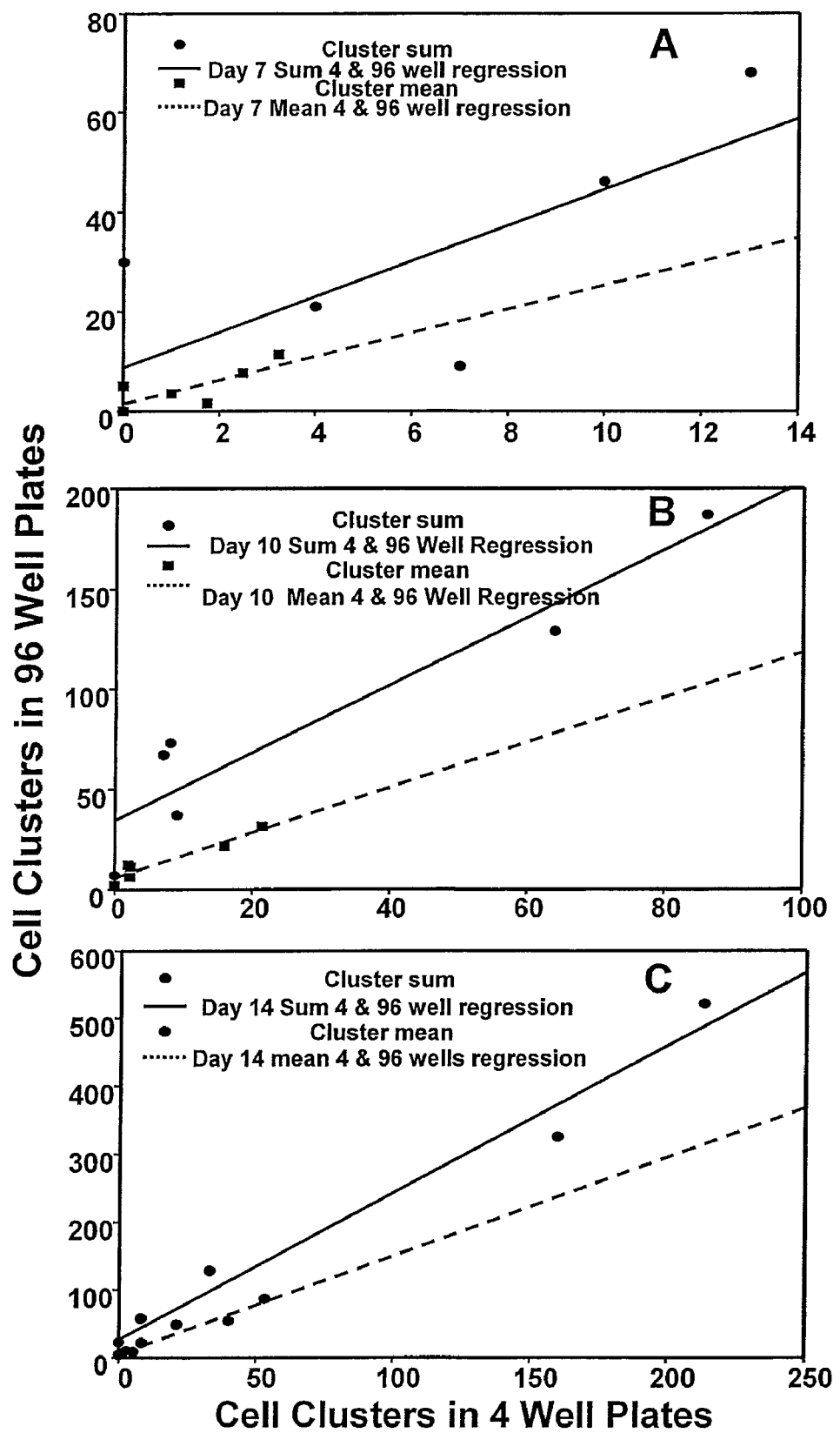
FIGS. 9A-9C show the correlation between the original manual 4-well assay and the 96-well assay, method of the present invention. The results were plotted as either the sum or mean of the replicates obtained on day 7 (FIG. 9A), day 10 (FIG. 9B) and day 14 (FIG. 9C) of culture.

To validate the 96-well plate assay, experiments using both assay systems were performed in parallel. A direct correlation exists between the 4-well and the 96-well plate assay, as shown in FIGS. 9A-9C and indicates that the results obtained from the latter have been validated.

Example 5

Use of High-Throughput Stem/Progenitor Cell Assays to Determine the Ability of a Test Compound to Modulate the Proliferation of Hematopoietic Stem and Progenitor Cells The HT-SPCA of the present invention is used to test dose responses for a variety of compounds that can interact with hematopoietic stem and progenitor cells. The agents either stimulate or inhibit and/or kill hematopoietic cells. Increasing doses of an agent can stimulate cells, but then be inhibitory by being toxic and causing necrosis. Other agents can be toxic at high doses, but induce apoptosis at lower concentrations.

Agents with known action on hematopoietic stem and progenitor cells include, 5-fluorouracil (5-FU), hydroxyurea, cytosine arabinoside (ara-C). busulphan, 3'azido-3'deoxythymide (AZT), cycloheximide, actinomycin D, etoposide, BCNU, doxorubicin, cisplatin (low hemotoxicity) and carboplatin. Growth factors known to inhibit the proliferation of stem and progenitor cells such as interferon-γ (IFNγ), tumor necrosis factor-α (TNF-α) and transforming growth factor-γ (TGFβ) are also tested. Neutraceuticals include, for example, the anti-inflammatory phytochemicals, black and green tea polyphenols, resveratrol, limonene and curcumin.

For these and other agents to be tested, mononuclear cells derived from peripheral blood, bone marrow and cord blood are used. CD34+ cells derived from these tissues can also be used. HT-SPCA assays for CFU-GEMM, GM-CFC, BFU-E, CFC-Mega and CFU-E, CFC-blast, HPP-CFC, M-CFC and G-CFC induced to proliferate and differentiate by contacting the cell populations with the appropriate cytokine of combinations of cytokines as given in Example 3, Table 1, above, are also performed.

HT-SPCA can be used to detect and predict hemotoxicity against hematopoietic stem and progenitor cell populations. To validate the inhibition/hemotoxicity of the agents, both manual CFA and the HT-SPCA are performed in parallel. One of the end points is to determine the IC50 and IC90 for the drug.

The invention claimed is:

1. A high-throughput assay method for rapidly identifying a compound capable of modulating the proliferative status of a population of primitive hematopoietic cells, comprising the steps of:
   (a) providing a first target cell population comprising primitive hematopoietic cells;
   (b) providing a plurality of second target cell populations comprising primitive hematopoietic cells;
   (c) incubating each of the first and the second target cell populations in a cell growth medium comprising fetal bovine serum having a concentration of between 0% and about 30%, methyl cellulose having a concentration of between about 0.4% and about 0.7%, and in an atmosphere having between about 3.5% oxygen and 7.5% oxygen;
   (d) contacting each of the first and the second target cell populations with a proliferation agent, the proliferation agent comprising one or more growth factors, one or more cytokines, or combinations thereof;
   (e) contacting the plurality of the second target cell populations with at least one test compound;
   (f) contacting each of the first and the second target cell populations with a reagent capable of reacting with ATP and generating luminescence in the presence of ATP;
   (g) detecting luminescence generated by the reagent that reacted with the ATP in each of the first and the second target cell populations, the level of luminescence indicating the amount of ATP in the first and the second target cell populations, wherein the amount of ATP indicates the proliferative status of the first and the second target cell populations of primitive hematopoietic cells; and
   (h) comparing the proliferative status of the plurality of the second target cell populations with the proliferative status of the first target cell population of primitive hematopoietic cells not in contact with the test compound, wherein a change in the proliferative status between the first target cell population and each one of the plurality of second target cell populations provides identification of a test compound capable of modulating the proliferative status of a target cell population.

2. The method of claim 1, wherein contacting each of the first and the second target cell populations of primitive hematopoietic cells with a proliferation agent generates cell populations substantially enriched in hematopoietic stem cells.

3. The method of claim 2, wherein the hematopoietic stem cells are selected from the group consisting of colony-forming cell-blast (CFC-blast), high proliferative potential colony forming cell (HPP-CFC), colony-forming unit-granulocyte, erythroid, macrophage, megakaryocyte (CFU-GEMM), and long-term culture-initiating cell (LTC-IC).

4. The method of claim 1, wherein contacting each of the first and the second target cell populations of primitive hematopoietic cells with a proliferation agent generates cell populations substantially enriched in at least one hematopoietic progenitor cell lineage.

5. The method of claim 4, wherein the at least one hematopoietic progenitor cell lineage is selected from the group consisting of granulocyte-macrophage colony-forming cell (GM-CFC), megakaryocyte colony-forming cell (CFC-mega), macrophage colony-forming cell (M-CFC), granulocyte colony forming cell (G-CFC), burst-forming unit erythroid (BFU-E), colony-forming unit-erythroid (CFU-E), colony-forming cell-basophil (CFC-Bas), colony-forming cell-eosinophil (CFC-Eo), colony-forming cell-megakaryocyte (CFC-Mega), B cell colony-forming cell (B-CFC) and T cell colony-forming cell (T-CFC).

6. The method of claim 1, wherein step (e) further comprises contacting each of the plurality of second target cell populations with at least two concentrations of the at least one test compound; and wherein step (h) further comprises calculating the IC50 of the at least one test compound.

7. The method of claim 1, wherein step (e) further comprises contacting each of the plurality of second target cell populations with at least two concentrations of the at least one test compound; and wherein step (h) further comprises calculating the IC90 of the at least one test compound.

8. The method of claim 1 wherein the proliferation agent is selected from the group consisting of erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, insulin, and combinations thereof.

9. The method of claim 1, wherein the concentration of fetal bovine serum is between about 0% and 10%.

10. The method of claim 1, wherein the concentration of methyl cellulose is about 0.7%.

11. The method of claim 1, wherein the concentration of oxygen in the atmosphere is about 5%.

12. The method of claim 1, wherein the reagent capable of reacting with ATP and generating luminescence in the presence of ATP comprises luciferin and luciferase.

13. The method of claim 12, wherein the population of primitive hematopoietic cells is isolated from an animal tissue selected from the group consisting of peripheral blood, bone marrow, umbilical cord blood, yolk sac, fetal liver, and spleen.

14. The method of claim 1, wherein the proliferation agent comprises erythropoietin, granulocyte-macrophage colony stimulating factor, granulocyte colony stimulating factor, stem cell factor, interleukin-3, interleukin-6, and optionally Flt3L, and wherein the proliferation agent generates a cell population substantially enriched in hematopoietic colony-forming unit-granulocyte, erythroid, macrophage, megakaryocyte (CFU-GEMM) stem cells.

15. The method of claim 1, wherein the proliferation agent comprises stem cell factor, interleukin-7, and Flt3L, and wherein the proliferation agent generates a cell population substantially enriched in colony-forming cells blast (CFC-Blast) stem cells.

16. The method of claim 1, wherein the proliferation agent comprises macrophage colony stimulating factor, interleukin-1, interleukin-3, interleukin-6, and stem cell factor, and wherein the proliferation agent generates a cell population substantially enriched in hematopoietic high proliferative potential colony-forming cell (HPP-CFC) stem cells.

17. The method of claim 1, wherein the proliferation agent is selected from the group consisting of erythropoietin, erythropoietin and interleukin-3, erythropoietin and stem cell factor and erythropoietin, stem cell factor and interleukin-3, and wherein the proliferation agent generates a cell population substantially enriched in the hematopoietic burst forming unit-erythroid (BFU-E) progenitor cells.

18. The method of claim 1, wherein the proliferation agent is selected from the group consisting of granulocyte-macrophage colony stimulating factor, granulocyte-macrophage colony stimulating factor and interleukin-3, and granulocyte-macrophage colony stimulating factor, interleukin-3 and stem cell factor, and wherein the proliferation agent generates a cell population substantially enriched in hematopoietic granulocyte-macrophage colony-forming cell (GM-CFC) progenitor cells.

19. The method of claim 1, wherein the proliferation agent is selected from the group consisting of thrombopoietin, and thrombopoietin, interleukin-3 and interleukin-6, and wherein the proliferation agent generates a cell population substantially enriched in the hematopoietic megakaryocyte colony-forming cell (CFC-Mega) progenitor cells.

20. The method of claim 1, wherein the proliferation agent is selected from the group consisting of interleukin-2, and interleukin-7, Flt3L and interleukin-15, and wherein the proliferation agent generates a cell population substantially enriched in the hematopoietic T cell colony forming cell (T-CFC) progenitor cells.

21. The method of claim 1, wherein the proliferation agent is selected from the group consisting of interleukin-7, and interleukin-7 and Flt3L, and wherein the proliferation agent generates a cell population substantially enriched in the hematopoietic B cell colony-forming cell (B-CFC) progenitor cells.

22. The method of claim 1, wherein the proliferation agent comprises erythropoietin and wherein the proliferation agent generates a cell population substantially enriched in the hematopoietic colony-forming unit-erythroid (CFU-E) progenitor cells.

23. The method of claim 1, wherein the proliferation agent is selected from the group consisting of granulocyte-colony stimulating factor and granulocyte-macrophage colony stimulating factor, and wherein the proliferation agent generates a cell population substantially enriched in the hematopoietic granulocyte colony-forming cell (G-CFC) progenitor cells.

24. The method of claim 1, wherein the proliferation agent is selected from the group consisting of interleukin-3, and interleukin-3 and stem cell factor, and wherein the proliferation agent generates a cell population substantially enriched in the hematopoietic colony-forming cell-Basophil (CFC-Bas) progenitor cells.

25. The method of claim 1, wherein the proliferation agent comprises granulocyte-macrophage colony stimulating factor, interleukin-3 and interleukin-5, and wherein the proliferation agent generates a cell population substantially enriched in the hematopoietic colony-forming cell-eosinophil (CFC-Eo) progenitor cells.

26. The method of claim 1, wherein the proliferation agent is selected from the group consisting of macrophage colony stimulating factor, macrophage colony stimulating factor and granulocyte-macrophage colony stimulating factor and interleukin-7, and granulocyte-macrophage colony stimulating factor, and wherein the proliferation agent generates a cell population substantially enriched in the hematopoietic macrophage colony-forming cell (M-CFC) progenitor cells.

27. The method of claim 1, wherein between step (e) and step (f), the method further comprises: (e1) incubating each of the first and the second target cell populations of primitive hematopoietic cells for a period of about 4 days.

28. The method of claim 1, wherein between step (e) and step (f), the method further comprises: (e1) incubating each of the first and the second target cell populations of primitive hematopoietic cells for a period of about 7 days.

29. The method of claim 1, wherein between step (e) and step (f), the method further comprises: (e1) incubating each of the first and the second target cell populations of primitive hematopoietic cells for a period of about 10 days.

30. The method of claim 1, wherein between step (e) and step (f), the method further comprises: (e1) incubating each of the first and the second target cell populations of primitive hematopoietic cells for a period of about 14 days.

* * * * *